US011022606B2

(12) United States Patent
Yoshikawa et al.

(10) Patent No.: US 11,022,606 B2
(45) Date of Patent: Jun. 1, 2021

(54) CELL INFORMATION ACQUISITION METHOD AND CELL INFORMATION ACQUISITION DEVICE

(71) Applicant: SYSMEX CORPORATION, Kobe (JP)

(72) Inventors: Keiko Yoshikawa, Kobe (JP); Yuma Oka, Kobe (JP); Shingo Fujiyama, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 332 days.

(21) Appl. No.: 15/791,456

(22) Filed: Oct. 24, 2017

(65) Prior Publication Data

US 2018/0113117 A1    Apr. 26, 2018

(30) Foreign Application Priority Data

Oct. 26, 2016   (JP) .............................. JP2016-210088

(51) Int. Cl.
*G01N 33/566*     (2006.01)
*G01N 33/53*      (2006.01)
(Continued)

(52) U.S. Cl.
CPC ..... *G01N 33/5041* (2013.01); *G01N 15/1459* (2013.01); *G01N 21/6428* (2013.01);
(Continued)

(58) Field of Classification Search
CPC ............. G01N 33/5041; G01N 33/566; G01N 15/1459; G01N 21/6428; G01N 33/53;
(Continued)

(56) References Cited

U.S. PATENT DOCUMENTS 10,145,794 B2 * 12/2018 Yoshikawa ........ G01N 15/1468
2014/0147860 A1 * 5/2014 Kaduchak ........ G01N 33/56966
435/7.21
2015/0374845 A1    12/2015 Muschler et al.

FOREIGN PATENT DOCUMENTS

JP    H08-313528 A    11/1996
JP    2005-315862 A   11/2005

OTHER PUBLICATIONS

Nissa L. Carrodus et al., "Differential Labeling of Cell-surface and Internalized Proteins after Antibody Feeding of Live Cultured Neurons", Journal of Visualized Experiments, Feb. 12, 2014, p. 1-6, Issue 84, e51139, Retrieved from http://www.jove.com/video/51139, Cited in the specification.
(Continued)

*Primary Examiner* — Gailene Gabel
(74) *Attorney, Agent, or Firm* — Metrolex IP Law Group, PLLC

(57) ABSTRACT

A cell information acquisition method may include: binding a binding substance to a receptor on a cell membrane surface of a cell, the binding substance being bindable to the receptor; permeabilizing a cell membrane of the cell after the binding; labeling a receptor in an intracellular area of the cell with a binding substance labeled with a first labeling substance after the permeabilizing; causing a specimen including the cell to flow through a flow path after the labeling; irradiating the cell included in the specimen flowing through the flow path with light; and acquiring a signal based on light generated from the first labeling substance in the cell irradiated with light.

15 Claims, 18 Drawing Sheets

(51) Int. Cl.
    *G01N 33/50*     (2006.01)
    *G01N 15/14*     (2006.01)
    *G01N 21/64*     (2006.01)
    *G01N 15/00*     (2006.01)
    *G01N 15/10*     (2006.01)

(52) U.S. Cl.
    CPC ........... *G01N 33/53* (2013.01); *G01N 33/566* (2013.01); *G01N 2015/0065* (2013.01); *G01N 2015/1006* (2013.01); *G01N 2021/6421* (2013.01); *G01N 2021/6439* (2013.01); *G01N 2333/705* (2013.01)

(58) Field of Classification Search
    CPC ..... G01N 2333/705; G01N 2015/1006; G01N 2015/0065; G01N 2021/6439
    See application file for complete search history.

(56) References Cited

OTHER PUBLICATIONS

Vorihisa Sakamoto et al., "Bovine apolipoprotein B-100 is a dominant immunogen in therapeutic cell populations cultured in fetal calf serum in mice and humans", Blood Journal, Jul. 15, 2007, p. 501-508, vol. 110, No. 2, The American Society of Hematology, Washington DC, USA, Retrieved from www.bloodjournal.org on Jun. 27, 2016.

Mads Lerdrup et al., "Geldanamycin stimulates internalization of ErbB2 in a proteasome-dependent way", Journal of Cell Science, 2006 (Accepted on Sep. 21, 2005), p. 85-95, vol. 119 (1), The Company of Biologists.

The Japanese Office Action dated Jun. 30, 2020 for the counterpart Japanese Patent Application No. 2016-210088, with English translation.

Office Action dated Mar. 23, 2021 in a counterpart Japanese patent application.

* cited by examiner

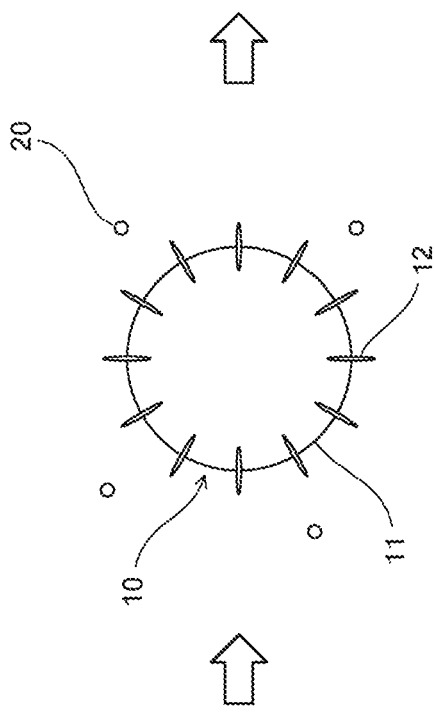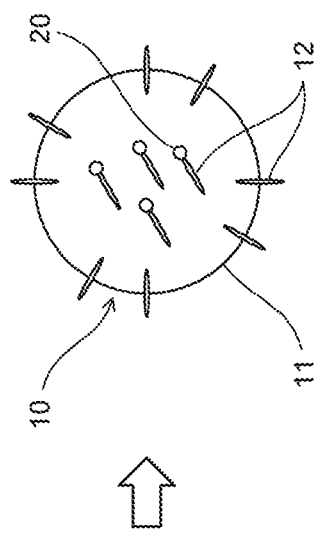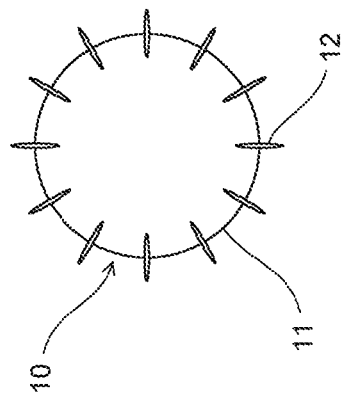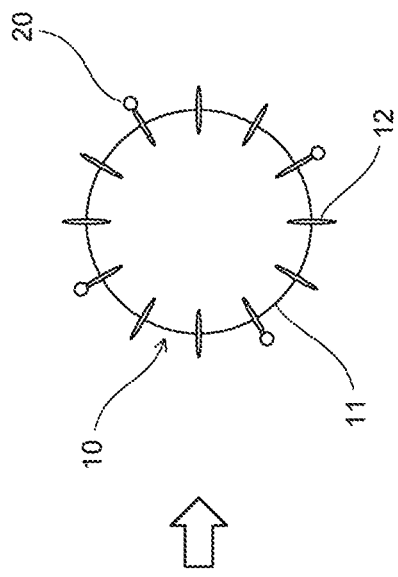

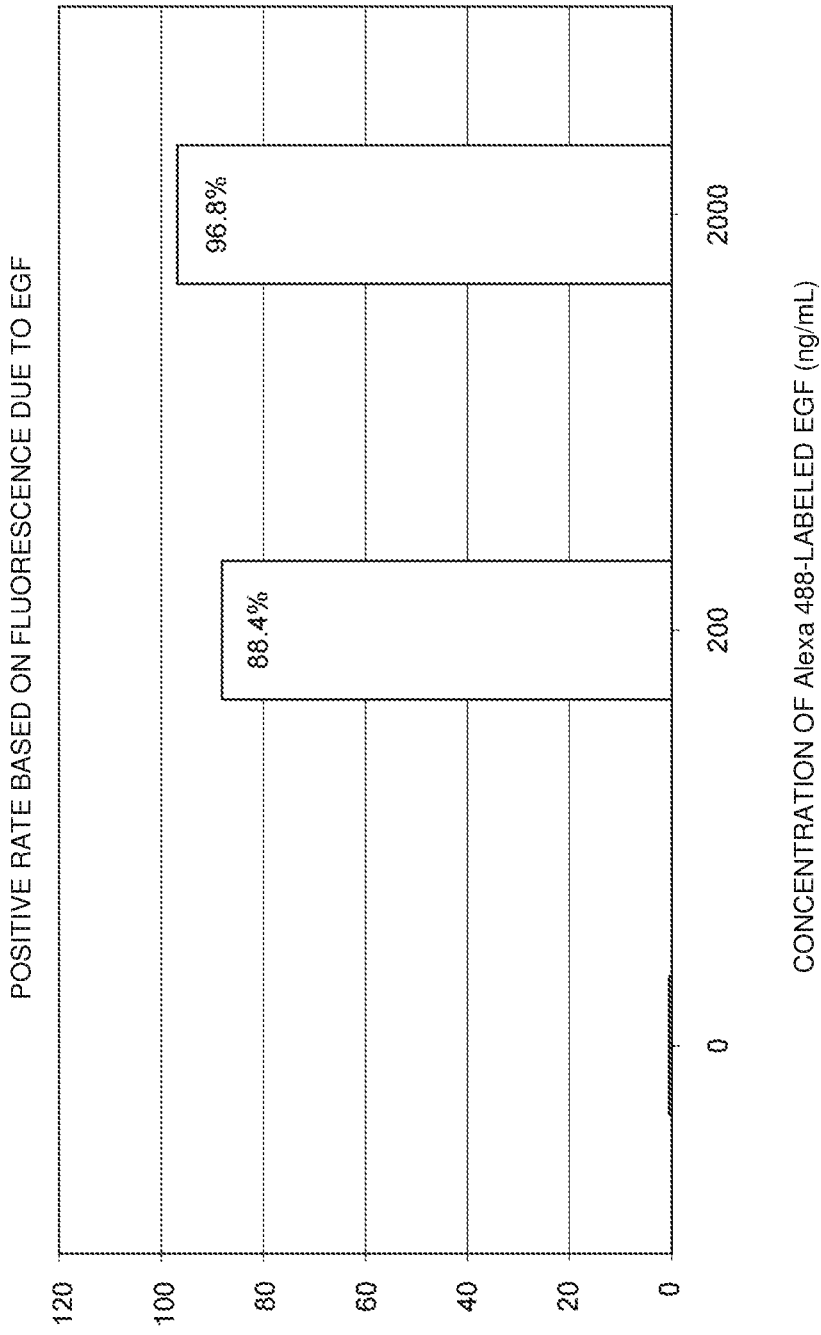

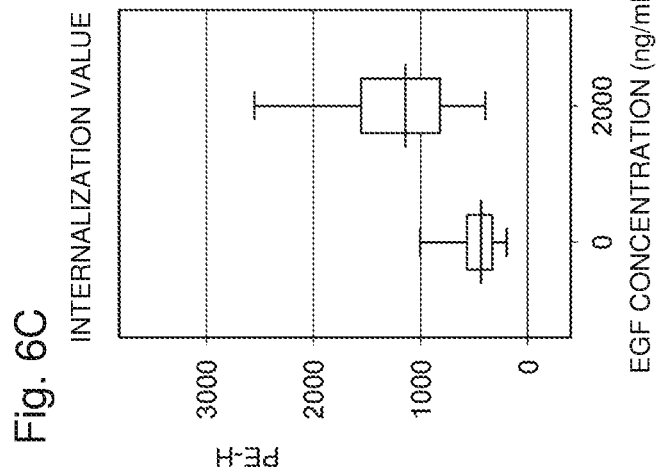
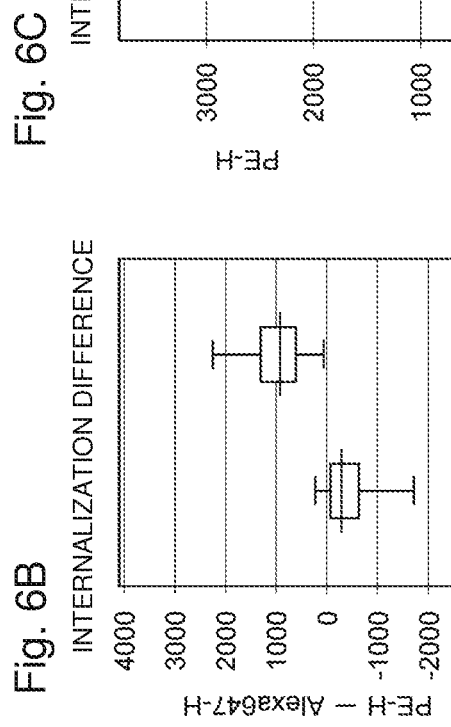
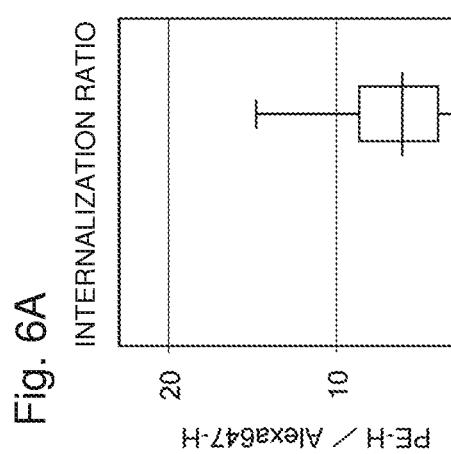

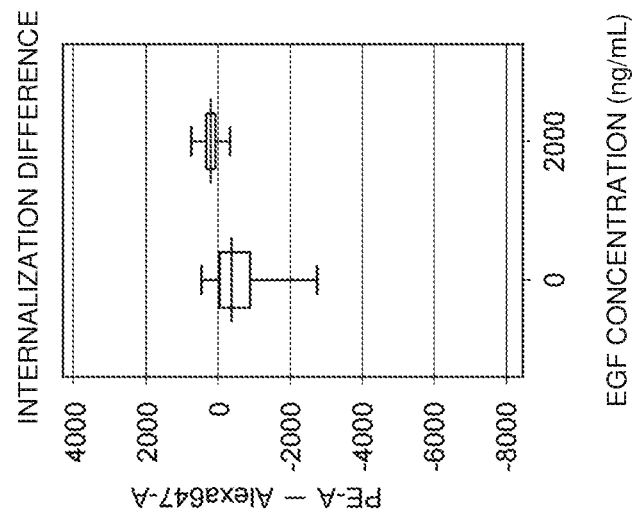
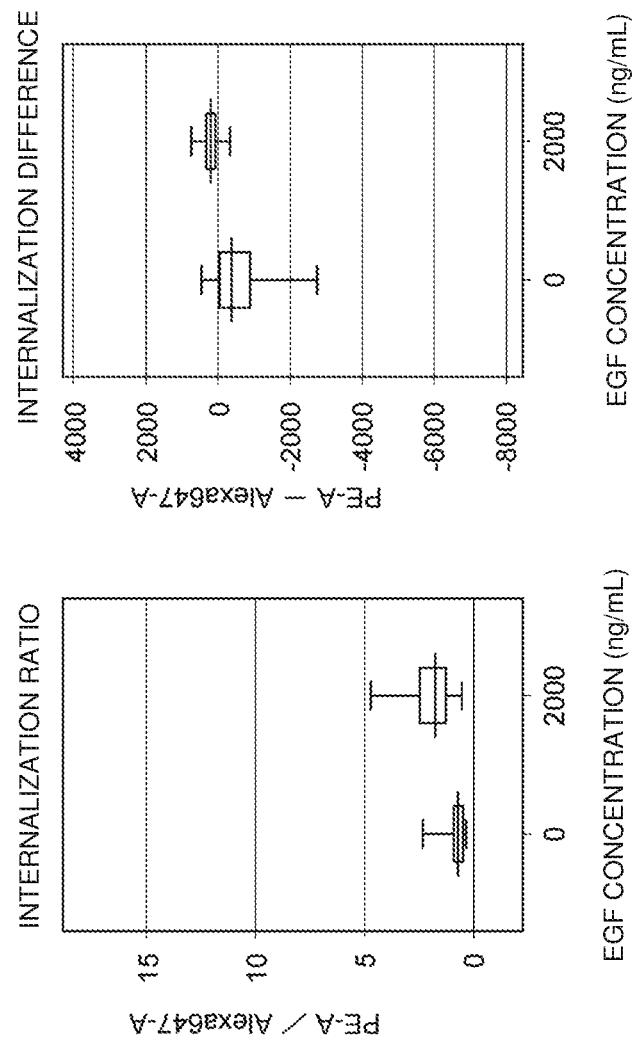

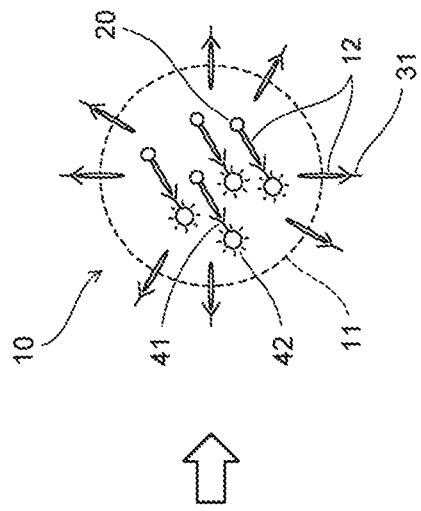
Fig. 12A BINDING
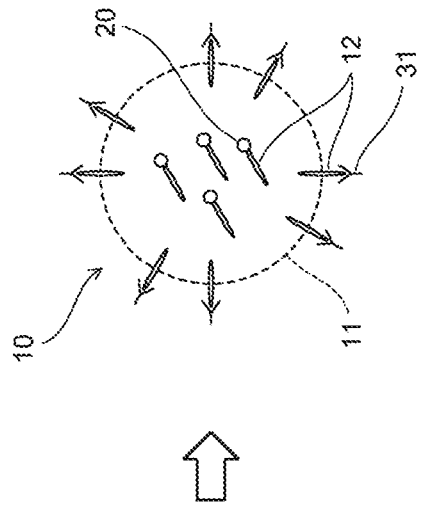
Fig. 12B PERMEABILIZATION
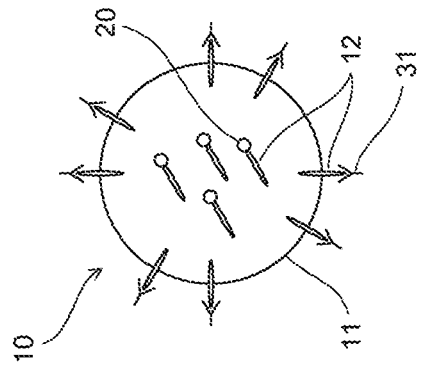
Fig. 12C LABELING
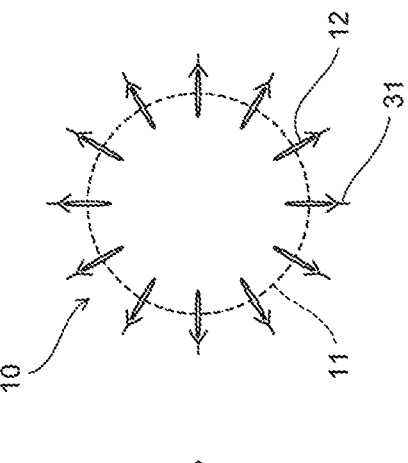
Fig. 12D BINDING
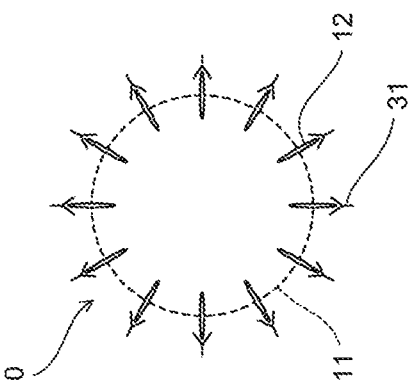
Fig. 12E PERMEABILIZATION
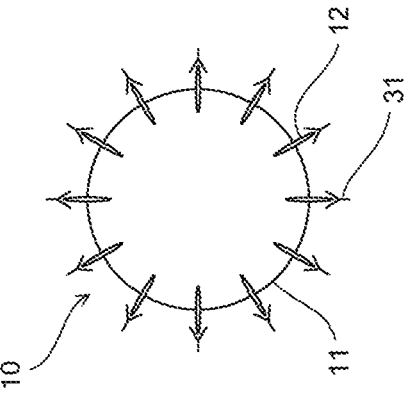
Fig. 12F LABELING

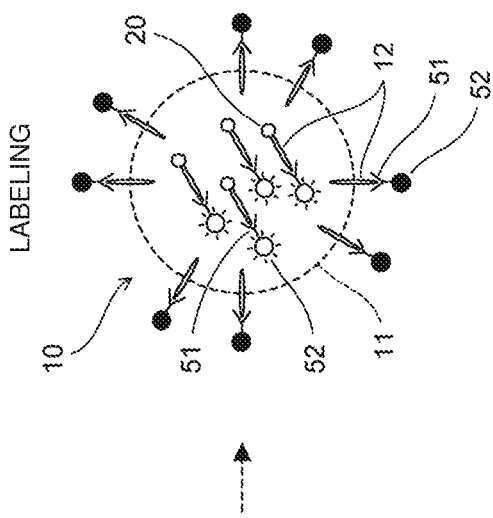
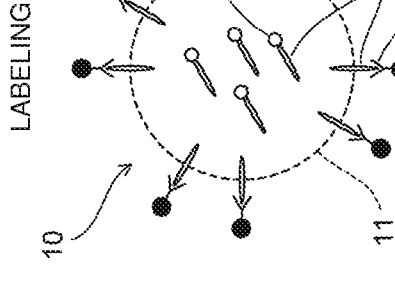
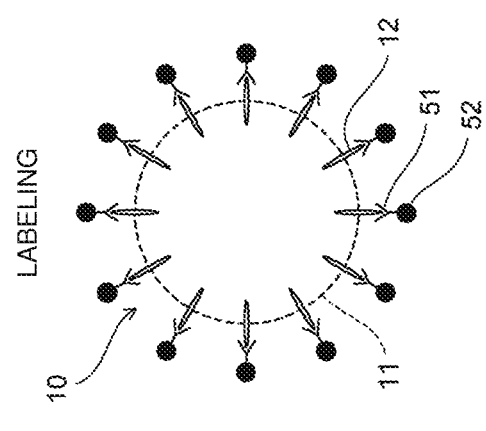
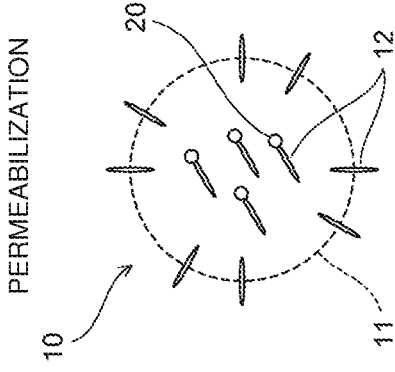
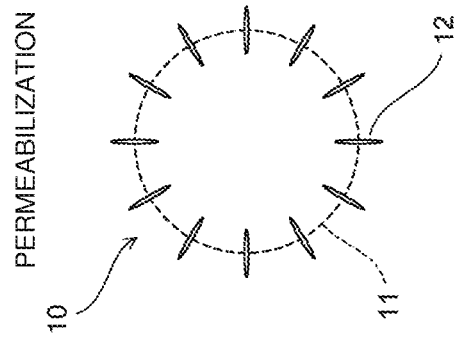

CELL INFORMATION ACQUISITION METHOD AND CELL INFORMATION ACQUISITION DEVICE

CROSS REFERENCE TO RELATED APPLICATIONS

This application claims priority from prior Japanese Patent Application No. 2016-210088 filed with the Japan Patent Office on Oct. 26, 2016, the entire contents of which are incorporated herein by reference.

BACKGROUND

The disclosure relates to a cell information acquisition method and a cell information acquisition device.

Various receptors present on a cell membrane surface specifically binds to a corresponding substance (ligand) such as a neurotransmitter, a hormone, and a cell growth factor, thereby transmitting a signal to the cell. Among the various receptors on a cell membrane surface, some receptors have been known to, after binding to ligands and transmitting signals, form complexes and be internalized in an intracellular area. It is expected to recognize the presence or absence of a ligand, and a biological reaction by analyzing the presence or absence of receptor internalization in intracellular area of the cell.

Nissa L. Carrodus et al., "Differential Labeling of Cell-surface and Internalized Proteins after Antibody Feeding of Live Cultured Neurons", Journal of Visualized Experiments 84, (the U.S.), Feb. 12, 2014, e51139, p. 1-6 (Non-Patent Literature 1) describes a method in which receptors 401 in a cell membrane surface each bind to an antibody 403 labeled with a first labeling substance 402 as illustrated in FIG. 18A, a cell membrane 404 is permeabilized, a receptor 401 in the intracellular area binds to an antibody 406 labeled with a second labeling substance 405 as illustrated in FIG. 18B, and the receptors 401 in the intracellular and extracellular areas are distinguished from each other and observed using a confocal microscope.

However, with the method described in Non-Patent Literature 1, receptors are visually detected for each of cells using a confocal microscope. Thus, it is difficult to efficiently recognize a receptor internalization state in a short time.

For instance, in a case where the effect of a molecular target drug targeted to receptors is monitored, an internalization state of the receptors, such as the number of cells in which a receptor is internalized through a cell membrane, and a ratio of the cells in which a receptor is internalized through a cell membrane to the cells in a sample may be useful indexes. However, the number of observable cells is limited due to visual check described in Non-Patent Literature 1. It takes significant time and effort to calculate the number of cells in which a receptor is internalized through a cell membrane, and a ratio of the cells in which a receptor is internalized through a cell membrane to the cells in a sample. In addition, in a case where target cells are rare cells such as circulating tumor cells (CTC), it is necessary to process a large amount of samples, for a great number of cells included in the large amount of samples, internalization of a receptor has to be identified for each of the cells. With the method described in Non-Patent Literature 1, the amount of samples for making measurements is limited, and it takes significant time and effort to visually identify an internalization state of a receptor into a cell membrane for each individual cell.

In consideration of such problems, one or more embodiments of the disclosure aim to provide a cell information acquisition method and a cell information acquisition device that are capable of efficiently detecting an internalization state of the receptors into a cell membrane in a cell.

SUMMARY

A cell information acquisition method according to one or more embodiments may include: binding a binding substance to a receptor on a cell membrane surface of a cell, the binding substance being bindable to the receptor; permeabilizing a cell membrane of the cell after the binding; labeling a receptor in an intracellular area of the cell with a binding substance labeled with a first labeling substance after the permeabilizing; causing a specimen including the cell to flow through a flow path after the labeling; irradiating the cell included in the specimen flowing through the flow path with light; and acquiring a signal based on light generated from the first labeling substance in the cell irradiated with light.

A cell information acquisition method according to one or more embodiments may include: permeabilizing a cell membrane of a cell; labeling a receptor with a binding substance which is bindable to the receptor and labeled with a labeling substance that generates light in a physiological environment in an intracellular area, after the permeabilizing; causing a specimen including the cell to flow through a flow path after the labeling; irradiating the cell included in the specimen flowing through the flow path with light; and acquiring a signal based on light generated from the labeling substance in the cell irradiated with the light.

A cell information acquisition device according to one or more embodiments may include: a specimen preparation part that prepares a specimen by performing operations including: binding a receptor on a cell membrane surface of a cell to a binding substance bindable to the receptor, permeabilizing a cell membrane of the cell for which the binding substance binds to the receptor on the cell membrane, and labeling, with a binding substance labeled with a first labeling substance, a receptor in an intracellular area of the cell for which the cell membrane is permeabilized; a flow cell through which the specimen flows; a light source that irradiates the specimen being flowing through the flow cell with light; and a light receiver that receives light generated from the first labeling substance and outputs a signal based on the light generated from the first labeling substance.

BRIEF DESCRIPTION OF DRAWINGS

FIG. 2A is a schematic diagram illustrating a cell to which no stimulus is applied;

FIG. 2B is a schematic diagram illustrating ligands around a cell;

FIG. 2C is a schematic diagram illustrating a binding of receptors and ligands;

FIG. 2D is a schematic diagram illustrating internalization of receptors in a cell according to a first embodiment;

FIG. 3A is a diagram illustrating a binding, FIG. 3B is a diagram illustrating a permeabilization and FIG. 3C is a diagram illustrating a labeling;

FIG. 3D is a diagram illustrating a binding, FIG. 3E is a diagram illustrating a permeabilization and FIG. 3F is a diagram illustrating a labeling;

FIG. 5 is a graph illustrating a result of determination of an internalization state acquired in advance preparation for verification in a first embodiment;

FIG. 6A is a graph illustrating an internalization ratio acquired by verification in a first embodiment;

FIG. 6B is a graph illustrating an internalization difference acquired by verification in a first embodiment;

FIG. 6C is a graph illustrating an internalization value acquired by verification in a first embodiment;

FIG. 6D a table illustrating an analysis result of a graph acquired based on FIG. 6A;

FIG. 6E is a table illustrating an analysis result of a graph acquired based on FIG. FIG. 6;

FIG. 6F is a table illustrating an analysis result of a graph acquired based on FIG. 6C;

FIG. 7A is a graph illustrating an internalization ratio acquired by verification in a modification of a first embodiment;

FIG. 7B is a graph illustrating an internalization difference acquired by verification in a modification of a first embodiment;

FIGS. 12A to 12C are each a schematic diagram illustrating a state where a cell with internalization of receptors is processed by applying a stimulus to the cell according to a second embodiment, and FIG. 12A is a diagram illustrating a binding, FIG. 12B is a diagram illustrating a permeabilization and FIG. 12C is a diagram illustrating a labeling;

FIGS. 12D to 12F are each a schematic diagram illustrating a state where a cell without internalization of receptors is processed with no stimulus applied to the cell according to a second embodiment, and FIG. 12D is a diagram illustrating a binding, FIG. 12E is a diagram illustrating a permeabilization and FIG. 12F is a diagram illustrating a labeling;

FIGS. 14A to 14C are each a schematic diagram illustrating a state where a cell with internalization of receptors is processed by applying a stimulus to the cell according to a third embodiment, and FIG. 14A is a diagram illustrating a binding, FIG. 14B is a diagram illustrating a permeabilization and FIG. 14C is a diagram illustrating a labeling;

FIGS. 14D and 14E are each a schematic diagram illustrating a state where a cell without internalization of receptors is processed with no stimulus applied to the cell according to a third embodiment, and FIG. 14D is a diagram illustrating a permeabilization and FIG. 14E is a diagram illustrating a labeling;

FIG. 18A is a diagram illustrating a labeling of a receptor in a cell membrane surface with a first labeling substance, and FIG. 18B is a diagram illustrating a labeling of a receptor in an intracellular area with a second labeling substance.

DETAILED DESCRIPTION

Figure 1:
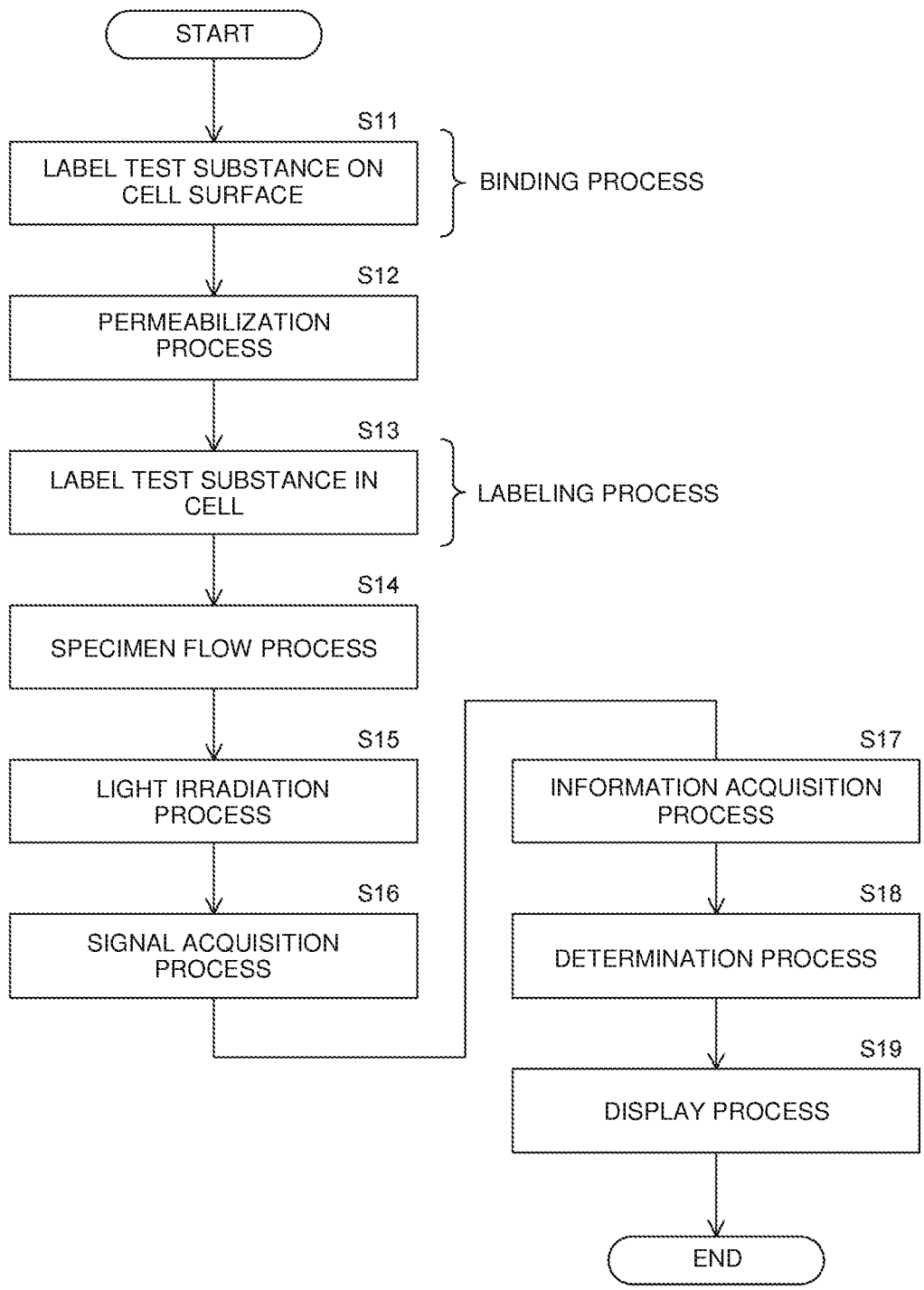
FIG. 1 is a flowchart illustrating a cell information acquisition method according to a first embodiment.

A first aspect of the disclosure relates to a cell information acquisition method. A cell information acquisition method may include: binding a binding substance to a receptor on a cell membrane surface of a cell, the binding substance being bindable to the receptor; permeabilizing a cell membrane of the cell after the binding; labeling a receptor in an intracellular area of the cell with a binding substance labeled with a first labeling substance after the permeabilizing; causing a specimen including the cell to flow through a flow path after the labeling; irradiating the cell included in the specimen flowing through the flow path with light; and acquiring a signal based on light generated from the first labeling substance in the cell irradiated with light.

A binding substance is one or multiple antibodies, for instance. A binding substance that binds to a receptor on a cell membrane surface and a binding substance that binds to a receptor in the intracellular area may be the same substance or may be different substances. The sentence "receptors on a cell membrane surface each bind to a binding substance" does not necessarily mean that all of the receptors on a cell membrane surface bind to a binding substance, and it is sufficient that at least part of the receptors on a cell membrane surface be bound to a binding substance. Also, the sentence "receptors in an intracellular area are labeled" does not necessarily mean that all of the receptors in an intracellular area are labeled, and it is sufficient that at least part of the receptors in the intracellular area be labeled.

In the cell information acquisition method according to this aspect, in a binding process, most of the receptors on a cell membrane surface each bind to a binding substance. Thus, in a labeling process performed after a permeabilization process, a large amount of binding substances binds to receptors in the intracellular area without binding to the receptors on the cell membrane surface. Therefore, receptors in the intracellular area are each labeled with a first labeling substance. Then a signal based on light generated from the first labeling substance is acquired. Since the acquired signal is based on the light generated from the first labeling substance, the signal indicates a receptor present in the intracellular area.

Thus, an internalization state of a receptor through a cell membrane in a cell can be efficiently detected with the acquired signal. This allows an internalization state of a receptor to be recognized, and the internalization state serves as an index, for instance, when the effect of a molecular target drug targeted to receptors is monitored. For instance, even when target cells are rare cells such as circulating tumor cells (CTC), a large amount of samples are measured by a flow cytometer, and an internalization state of the receptors in each individual cell can be efficiently detected. Consequently, the time and effort of an operator can be reduced.

The cell information acquisition method according to this aspect may further include an information acquisition process (S17) of acquiring information on the height of the waveform of the signal based on the acquired signal, the information indicating an internalization state of the receptors (12) through the cell membrane (11) in the cells (10). When receptors are internalized from a cell membrane surface into an intracellular area, the receptors aggregate in the intracellular area. Also, the height of the waveform of the signal increases particularly when the receptors aggregate. Therefore, when receptors aggregate and are internalized in the intracellular area, acquisition of information on the height of a signal waveform as information indicating an internalization state enables the internalization state of the receptors in the intracellular area to be detected with higher accuracy.

Here, in the binding process, all the receptors on a cell membrane surface do not necessarily each bind to a binding substance, and, for instance, part, that is, approximately one-tenth of the receptors may remain unbound. In this case, when the receptors which are internalized in the intracellular area are attempted to be labeled in the labeling process, unbound receptors on the cell membrane surface are each labeled with the first labeling substance, and light generated from the first labeling substance which labels a receptor on the cell membrane surface is noise. However, as described above, the height of the waveform of the signal increases particularly when receptors are internalized and aggregate. Thus, with the information on the height of the waveform of the signal, a signal based on the internalized receptors and a signal based on the noise generated from the cell membrane surface can be distinguished with high accuracy. Thus, an internalization state of the receptors in an intracellular area can be detected with high accuracy.

It is to be noted that information on the area or width of the waveform of a signal may be acquired as the information indicating an internalization state. However, when receptors are internalized in the intracellular area and aggregate, the height of the waveform of the signal particularly increases. Thus, as described above, it may be preferable to acquire the information on the height of the waveform of the signal as the information indicating an internalization state.

In the cell information acquisition method according to this aspect, the signal may be an electrical signal outputted by a light receiver (221) based on the light generated from the first labeling substance (42). The electrical signal is a signal such as a current or a voltage outputted by the light receiver, for instance.

In the cell information acquisition method according to this aspect, a binding substance (31) binding to the receptor (12) on the cell membrane (11) surface may be labeled with a second labeling substance (32) that generates light with a second wavelength ($\Delta 22$) different from light with a first wavelength ($\Delta 21$) generated by the first labeling substance (42). In this case, in the cell information acquisition method according to this aspect, a signal based on the light with the second wavelength ($\Delta 22$) may be acquired by the irradiation of the cells (10) with light. Since the signal based on the light with the second wavelength is a signal based on the light generated from the second labeling substance which labels a receptor on the cell membrane surface, the signal indicates the receptor present on the cell membrane surface. Also, when receptors are internalized from the cell membrane surface into the intracellular area, the number of receptors on the cell membrane decreases, and the number of receptors in the intracellular area increases. Thus, an internalization state of the receptors in a cell can be detected with high accuracy by the signal based on the light with the first wavelength and the signal based on the light with the second wavelength.

In this case, the cell information acquisition method according to this aspect may further include an information acquisition process (S17) of acquiring the ratio or the difference between information on a height of a waveform of the signal based on the light with the first wavelength ($\lambda 21$), and information on a height of a waveform of the signal based on the light with the second wavelength ($\lambda 22$) using the acquired signal based on the light with the first wavelength ($\lambda 21$) and the acquired signal based on the light with the second wavelength ($\lambda 22$), the information indicating an internalization state of the receptors (12) through the cell membrane (11) in the cells (10). In a cell in which receptors are internalized in the intracellular area, the receptors aggregate, and thus the height of the waveform of the signal based on the light with the first wavelength corresponding to the receptors in the intracellular area increases. On the other hand, in a cell in which receptors are not internalized in the intracellular area, the receptors are not likely to aggregate, the height of the waveform of the signal based on the light with the second wavelength corresponding to the receptors on the cell membrane surface is lower than the height of the waveform of the signal based on the light with the first wavelength when receptors aggregate. Like this, the height of the waveform of the signal based on the light with the first wavelength and the height of the waveform of the signal based on the light with the second wavelength characteristically vary according to an internalization state of the receptors. Therefore, internalization state of receptors through the cell membrane tends to reflect on the ratio or the difference between the heights of two signal waveforms. Consequently, an internalization state of the receptors through the cell membrane can be detected with high accuracy.

It is to be noted that in the information acquisition process, the ratio or the difference between information on the area of the waveform of the signal based on the light with the first wavelength ($\lambda 21$), and information on the area of the waveform of the signal based on the light with the second wavelength ($\lambda 22$) may be acquired using the acquired signal based on the light with the first wavelength ($\lambda 21$) and the acquired signal based on the light with the second wavelength ($\lambda 22$), the information indicating an internalization state of the receptors through the cell membrane in the cells. However, in contrast to the difference between the height of the waveform of the signal based on the light with the first wavelength and the height of the waveform of the signal based on the light with the second wavelength, the difference between the area of the waveform of the signal based on the light with the first wavelength and the area of the waveform of the signal based on the light with the second wavelength is unlikely to occur, and the difference between the width of the waveform of the signal based on the light with the first wavelength and the width of the waveform of the signal based on the light with the second wavelength is unlikely to occur. Therefore, in the information acquisition process, it may be preferable to acquire the ratio or the difference between information on the height of the waveform of the signal based on the light with the first wavelength, and information on the height of the waveform of the signal based on the light with the second wavelength.

In the cell information acquisition method according to this aspect, the signal based on the light with the second wavelength (λ22) may be an electrical signal outputted by a light receiver (222) based on light generated from the first labeling substance (32) that generates the light with the second wavelength (λ22). The electrical signal is, for instance, a signal such as a current or a voltage outputted by the light receiver.

The cell information acquisition method according to this aspect may further include a display process (S19) of displaying the information indicating an internalization state of the receptors (12) through the cell membrane (11) in the cells (10). In this manner, a degree of internalization for each cell can be smoothly and visually recognized.

The cell information acquisition method according to this aspect may further include a determination process (S18) of determining whether internalization of the receptors (12) through the cell membrane is present or absent for each of the cells (10) based on the information indicating an internalization state of the receptors (12) through the cell membrane (11) in the cells (10). In this manner, whether internalization of the receptor through the cell membrane is present or absent can be smoothly determined for each of the cells. Also, after presence or absence of internalization of the receptor through the cell membrane is determined, when the receptor is a target of a molecular target drug, a result of the determination can be used for drug effect monitoring. Also, a target receptor is set to a receptor for a bacterial disease or a receptor for a viral disease, and it is thereby possible to know whether a subject suffers from a bacterial disease or a viral disease based on a result of the determination.

In this case, the cells (10) are each a cell in blood obtained from a subject to whom a molecular target drug targeted to the receptors (12) is administered. In this manner, the effect of the molecular target drug on a subject can be monitored.

In the cell information acquisition method according to this aspect, in the determination process (S18), whether internalization of the receptors (12) through the cell membrane is present or absent may be determined by comparing the information indicating an internalization state with a predetermined threshold value. In this manner, whether internalization of the receptor through the cell membrane is present or absent can be clearly determined for each of the cells according to the information indicating an internalization state.

The cell information acquisition method according to this aspect may further include a display process (S19) of displaying presence or absence of internalization of the receptors (12) through the cell membrane determined for each of the cells (10) in the determination process (S18). In this manner, presence or absence of internalization determined for each of the cells can be smoothly and visually recognized.

In the cell information acquisition method according to this aspect, in the determination process (S18), the number of the cells (10), in which a receptor (12) are internalized through the cell membrane (11), may be acquired. In this manner, evaluation of the effect of a molecular target drug and determination of presence or absence of extracellular stimulus can be smoothly made.

The cell information acquisition method according to this aspect may further include a display process (S19) of displaying the number of the cells (10) which is acquired in the determination process (S18) and in which a receptor (12) is internalized through the cell membrane (11). In this manner, the number of the cells in which the receptor is internalized through the cell membrane can be smoothly and visually recognized.

In the cell information acquisition method according to this aspect, in the determination process (S18), whether extracellular stimulation is present or absent may be determined based on the number of the cells (10) in which a receptor (12) is internalized through the cell membrane (11). In this manner, whether extracellular stimulation is present or absent can be smoothly determined.

In the cell information acquisition method according to this aspect, in the determination process (S18), the ratio of the cells (10) in which a receptor (12) is internalized through the cell membrane (11) to the cells (10) in which presence or absence of internalization of the receptor (12) through the cell membrane is determined may be acquired. In this manner, evaluation of the effect of a molecular target drug and determination of presence or absence of extracellular stimulus can be smoothly made.

The cell information acquisition method according to this aspect may further include a display process (S19) of displaying the ratio of the cells (10) in which a receptor (12) is internalized through the cell membrane (11), acquired in the determination process (S18). In this manner, the ratio of the cells in which a receptor is internalized through the cell membrane to the total of cells can be smoothly and visually recognized.

In the cell information acquisition method according to this aspect, in the determination process (S18), whether extracellular stimulation is present or absent may be determined based on the ratio of the cells (10) in which a receptor (12) is internalized through the cell membrane (11). In this manner, whether extracellular stimulation is present or absent can be smoothly determined.

The cell information acquisition method according to this aspect may further include a display process (S19) of displaying presence or absence of the extracellular stimulation determined in the determination process (S18). In this manner, presence or absence of the extracellular stimulation can be smoothly and visually recognized.

The cell information acquisition method according to this aspect may further include a process (S41) of acquiring images (321, 322, 323) of the cells (10) included in the specimen flowing through the flow path (201). In this manner, for instance, an internalization state of the receptors in the cells can be checked by referring to the images. Also, whether internalization of a receptor through the cell membrane is present or absent in each cell can also be determined by analyzing the images. However, when the presence or absence of internalization of a receptor through the cell membrane is attempted to be determined by image analysis, and a large amount of samples are processed, the image analysis needs to be performed for a significant number of cells. In this case, an excessive load is applied to a processor that performs the image analysis. Therefore, it may be preferable to detect an internalization state of the receptors in each cell based on the light generated from the labeling substance.

A second aspect of the disclosure relates to a cell information acquisition method. A cell information acquisition method may include: permeabilizing a cell membrane of a cell; labeling a receptor with a binding substance which is bindable to the receptor and labeled with a labeling substance that generates light in a physiological environment in an intracellular area, after the permeabilizing; causing a specimen including the cell to flow through a flow path after the labeling; irradiating the cell included in the specimen flowing through the flow path with light; and acquiring a signal based on light generated from the labeling substance in the cell irradiated with the light.

As described later, a first labeling substance that generates light in a physiological environment in the intracellular area may not only generate light in pH in the intracellular area, but also may generate light at a temperature in the intracellular area or at an oxygen partial pressure in the intracellular area, or may generate light by reacting to a substance in the intracellular area, for instance. The acquired signal is, for instance, an electrical signal outputted by the light receiver based on the light generated from the first labeling substance.

The cell information acquisition method according to this aspect both receptors in the intracellular area and receptors on the cell membrane surface are labeled with the labeling substance. In this process, out of the labeling substances in the intracellular area and on the cell membrane surface, only the labeling substance that labels a receptor in the intracellular area generates light. Also, a signal based on the light generated from the labeling substance is acquired. Since the acquired signal is a signal based on the light generated from the labeling substance that labels a receptor in the intracellular area, the signal indicates a receptor present on the cell membrane surface. Consequently, as in the first aspect, an internalization state of the receptors from the cell membrane surface through the cell membrane in each cell can be efficiently detected by the acquired signal, and the time and effort of an operator can be reduced.

In this case, the first labeling substance (52) may be configured to generate light according to pH in the intracellular area. Normally, pH in a cell membrane is different from pH outside the cell. Therefore, when the first labeling substance is configured to generate light according to pH in the intracellular area, only the labeling substance that labels a receptor in the intracellular area generates light, and thus an internalization state of the receptors in the intracellular area can be detected reliably.

A third aspect relates to a cell information acquisition device (100). A cell information acquisition device may include: a specimen preparation part that prepares a specimen by performing operations including: binding a receptor on a cell membrane surface of a cell to a binding substance bindable to the receptor, permeabilizing a cell membrane of the cell for which the binding substance binds to the receptor on the cell membrane, and labeling, with a binding substance labeled with a first labeling substance, a receptor in an intracellular area of the cell for which the cell membrane is permeabilized; a flow cell through which the specimen flows; a light source that irradiates the specimen being flowing through the flow cell with light; and a light receiver that receives light generated from the first labeling substance and outputs a signal based on the light generated from the first labeling substance.

The light receiver is a light detector, for instance. With a cell information acquisition device according to the third aspect, the same effect as in the first aspect is achieved.

In the cell information acquisition device (100) according to this aspect, the specimen preparation part (130) may label a receptor (12) on the cell membrane surface (11) by a second labeling substance (32) that generates light with a second wavelength (λ22) different from light with a first wavelength (λ21) generated by the first labeling substance (42). In this case, the light receiver (221, 222) may receive the light with the second wavelength (λ22), and may output a signal based on the light with the second wavelength (λ22).

According to one or more aspects, an internalization state of the receptors through the cell membrane in a cell can be efficiently detected.

First Embodiment

A first embodiment relates to a cell information acquisition method of labeling receptors present on a cell membrane surface and receptors present in an intracellular area with labeling substances and of determining whether internalization state of receptors in the intracellular area is present or absent based on the fluorescence generated from the labeled substance. A receptor is activated by binding to a corresponding ligand, for instance, and is internalized from a cell membrane surface through the cell membrane. In a first embodiment, receptors on a cell membrane surface and receptors in an intracellular area are labeled with the respective labeling substances that generate fluorescence with different wavelengths. A fluorescence generated from each labeled substance is received by flow cytometry, and information indicating an internalization state of the receptors in each cell is acquired based on the received fluorescence.

As a receptor and a ligand which are internalized by binding to each other, combinations of the receptor and the ligand include, for instance, an epidermal growth factor receptor (EGFR) and an EGF.

The combination of the receptor and the ligand which bind to each other and then are internalized is not limited to EGFR and EGF. For instance, in the case of a combination of a tyrosine kinase-type receptor to which EGFR belongs and a ligand, the combinations of a receptor and a ligand include a PDGFR and a platelet-derived growth factor (PDGF), a VEGFR and vascular endothelial growth factor (VEGF), and a FGF2R and a fibroblast growth factor (FDF). For instance, in the case of a combination of a G protein coupled receptor (GPCR) and a ligand, combinations of a receptor and a ligand include an MCHR1 and a melanin-concentrating hormone (MCH). In addition, combinations of a receptor and a ligand include a P2Y12 receptor and an ADP, and an erythropoietin receptor and erythropoietin.

As illustrated in FIG. 1, the cell information acquisition method in a first embodiment includes processes S11 to S19. Step S11 is a binding process and step S13 is a labeling process. Hereinafter, a case is described, in which an operator prepares the specimen, and the cell information acquisition method of FIG. 1 is performed using a flow cytometer that receives fluorescence generated from the prepared specimen, and an analysis device for analyzing a signal outputted from the flow cytometer. The steps of FIG. 1 may be performed by processing in a cell information acquisition device. The device configuration in a case where the steps of FIG. 1 are performed by the cell information acquisition device is described later with reference to FIGS. 8 to 10.

The internalization of receptors in a cell is described with reference to FIGS. 2A to 2D.

As illustrated in FIG. 2A, in a condition in which no stimulus is applied to a cell 10, receptors 12 are distributed over a cell membrane 11, that is, a cell membrane surface. As illustrated in FIG. 2B, ligands 20 corresponding to the receptors 12 appear around the cell 10. As illustrated in FIG. 2C, the receptors 12 binds to the ligands 20, which makes the cell 10 receive a stimulus. Subsequently, as illustrated in FIG. 2D, the receptors 12 binding to the ligands 20 are internalized in the cell 10, in other words, an intracellular area. In this manner, a signal outside of the cell 10 is transmitted to the inside of the cell 10.

For instance, in a case where the receptor 12 and the ligand 20 are respectively EGFR and EGF, when EGF is secreted as a stimulating substance, EGF binds to EGFR on the cell membrane surface. Then, a complex of EGFR and EGF is internalized into the intracellular area. In the case where the receptor 12 and the ligand 20 have another combination, a complex is internalized through the cell membrane similarly. It is to be noted that the receptor 12 and the ligand 20 binding to each other and internalized in the intracellular area are transported to the endosome, and are decomposed by the lysosome.

Figure 3A:
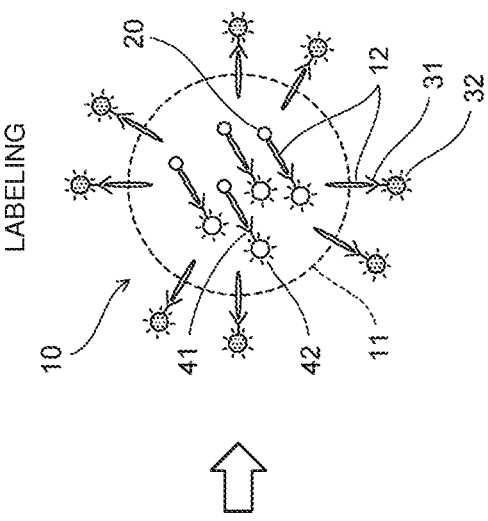
FIGS. 3A to 3C are each a schematic diagram illustrating a state where a cell with internalization of receptors is processed by applying a stimulus to the cell according to a first embodiment.
Figure 3B:
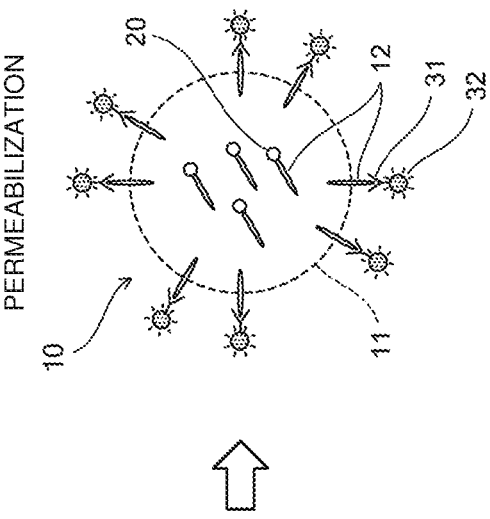
Figure 3C:
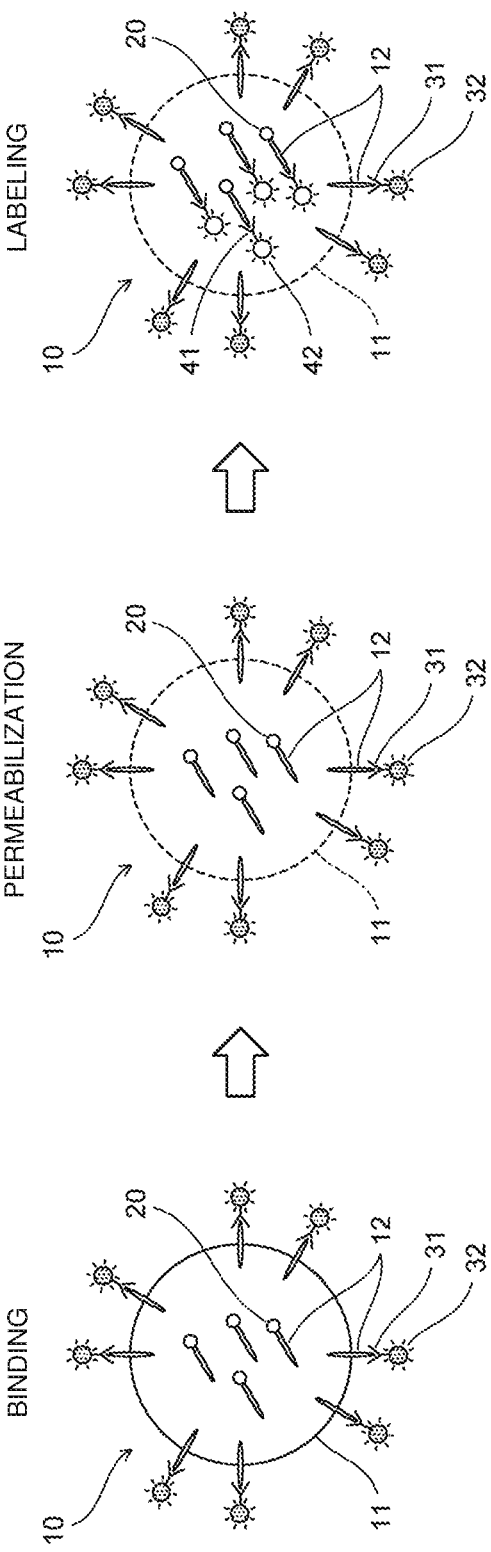
Figure 3D:
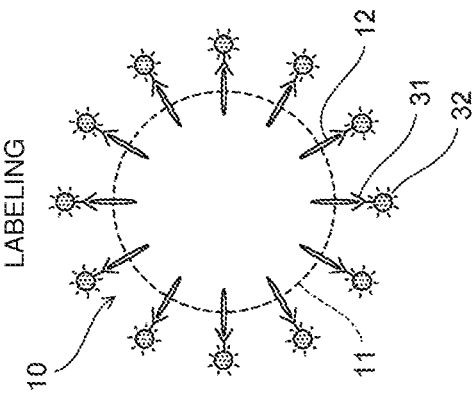
FIGS. 3D to 3F are each a schematic diagram illustrating a state where a cell without internalization of receptors is processed with no stimulus applied to the cell according to a first embodiment.
Figure 3E:
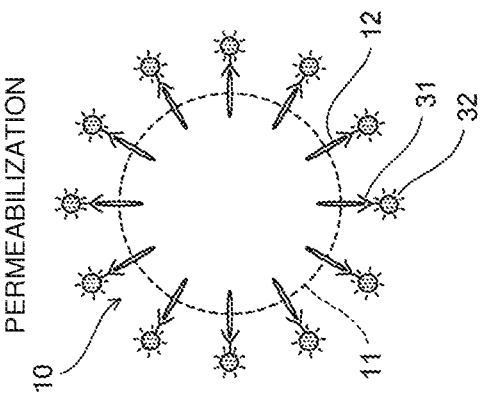
Figure 3F:
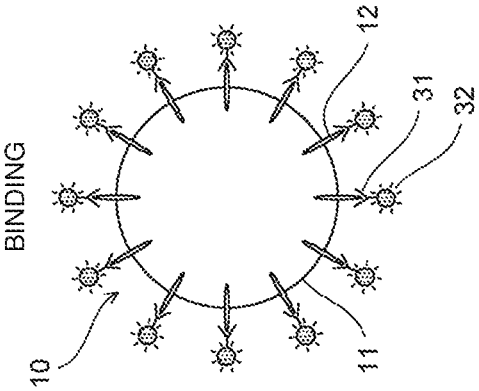

Returning to FIG. 1, the steps S11 to S19 are described with reference to FIGS. 3A to 3F as needed. FIGS. 3A to 3C are each a diagram illustrating a process state of a cell in which internalization of receptor 12 is caused with a stimulus applied to the cell 10. FIGS. 3D to 3F are each a diagram illustrating a process state of a cell in which no internalization of receptors 12 is caused without any stimulus applied to the cell 10.

In step S11, the operator performs the binding process for labeling the receptor 12 on the cell membrane surface. Specifically, as illustrated in FIGS. 3A and 3D, the operator brings binding substances 31 into contact with the cell 10, and let each binding substance 31 bind to a receptor 12 on the cell membrane surface. The binding substance 31 is a substance bindable to the receptor 12, and is, for instance, an antibody that specifically binds to the receptor 12. Also, the binding substance 31 is labeled with a labeling substance 32. The labeling substance 32 is a fluorescent substance that generates fluorescence when being irradiated with light with a predetermined wavelength. When the receptor 12 on the cell membrane surface binds to the binding substance 31 in the binding process in step S11, the receptor 12 on the cell membrane surface is labeled with the labeling substance 32 via the binding substance 31.

It is to be noted that the binding substance 31 may be composed of multiple antibodies. The sentence "receptors 12 on a cell membrane surface each bind to the binding substance 31" does not necessarily mean that all of the receptors 12 on a cell membrane surface bind to the binding substance 31, and it is sufficient that at least part of the receptors 12 on a cell membrane surface bind to the binding substance 31.

In step S12, the operator performs permeabilization process for the cell membrane 11 of the cell 10. Thus, the cell membrane 11 of the cell 10 illustrated in FIGS. 3A and 3D becomes a permeable state as illustrated with a dashed line in FIGS. 3B and 3E. In subsequent step S13, the permeabilization process enables a binding substance 41 labeled with a labeling substance 42 to enter an intracellular area from an extracellular area through the cell membrane 11.

In step S13, the operator performs the labeling process of labeling the receptors 12 in the intracellular area using the binding substance 41. Specifically, as illustrated in FIG. 3C, the operator sends the binding substance 41 labeled with the labeling substance 42 into the intracellular area through the cell membrane 11. The operator then brings the binding substance 41 into contact with the cell 10, and let the binding substance 41 bind to the receptors 12 in the intracellular area. The binding substance 41 is a substance bindable to the receptor 12, and is, for instance, an antibody that specifically binds to the receptor 12. The labeling substance 42 is a fluorescent substance that generates fluorescence with a wavelength different from the fluorescence generated by the labeling substance 32 when being irradiated with light with a predetermined wavelength.

Here, the portion of the receptor 12 recognized by the binding substance 41 is the same as the portion of the receptor 12 recognized by the binding substance 31. When the recognition portion of the binding substance 41 is the same as the recognition portion of the binding substance 31, the binding substance 41 and the binding substance 31 may be the same substance or may be different substances.

For the cell 10 in which receptors 12 are internalized through the cell membrane as illustrated in FIG. 3C, the receptors 12 in the intracellular area is labeled with the labeling substance 42 via the binding substance 41 by the labeling process in step S13. On the other hand, for the cell 10 in which no receptors 12 are internalized through the cell membrane as illustrated in FIG. 3F, the intracellular area is not labeled with the labeling substance 42.

It is to be noted that the binding substance 41 may be composed of multiple antibodies. Also, the sentence "receptors 12 in an intracellular area are labeled" does not necessarily mean that all of the receptors 12 in an intracellular area are labeled, and it is sufficient that at least part of the receptors 12 in an intracellular area be labeled.

In steps S14 to S16, the operator performs a process of acquiring a first signal based on the fluorescence generated from the labeling substance 42, and acquiring a second signal based on the fluorescence generated from the labeling substance 32 by a flow cytometry method.

In step S14, the operator supplies a specimen including the cell 10 which has undergone steps S11 to S13 to the flow cytometer. The flow cytometer passes the supplied specimen to the flow path of a flow cell. In step S15, the flow cytometer irradiates the specimen which flows through the flow path of the flow cell with light to generate fluorescence from the labeling substances 32, 42. Consequently, the cell 10 included in the specimen is irradiated with light, and fluorescence with different wavelengths are generated from the labeling substances 32, 42. In step S16, the flow cytometer receives the fluorescence, which is generated from the labeling substances 32, 42 due to irradiation of the cell 10 with light, by the light receiver. The light receiver outputs the first signal based on the fluorescence generated from the labeling substance 42 and the second signal based on the fluorescence generated from the labeling substance 32. The first signal and the second signal are wave-like signals. In this manner, the operator acquires the first signal and the second signal by using the flow cytometer.

By the processing in steps S11 to S16, most receptors 12 on the cell membrane surface each bind to a binding substance 31 in the binding process. Thus, in the labeling process performed after the permeabilization process, a large amount of binding substances 41 bind to receptors 12 in the intracellular area without binding to the receptors 12 on the cell membrane surface. Therefore, receptors 12 in the intracellular area are each labeled with a labeling substance 42. In step S16, the first signal based on the light generated from the labeling substance 42 is acquired. Since the first signal is based on the light generated from the labeling substance 42, the first signal indicates a receptor 12 present in the intracellular area.

Thus, an internalization state of the receptors 12 in the intracellular area in each cell can be efficiently detected with the first signal. For instance, even in a case where target cells are rare cells such as circulating tumor cells (CTC), a large amount of samples are measured by a flow cytometer, and an internalization state of the receptors 12 in each individual cell can be efficiently detected. Consequently, the time and effort of the operator can be reduced.

Also, in the binding process, a receptor 12 on the cell membrane surface binds to the binding substance 31, thereby being labeled with the labeling substance 32. Then in step S16, the second signal based on the light generated from the labeling substance 32 along with the first signal is acquired. Since the second signal is based on the light generated from the labeling substance 32, the second signal indicates a receptor 12 present on the cell membrane surface. Also, when receptors 12 are internalized from the cell membrane surface into the intracellular area, the number of receptors 12 on the cell membrane decreases, and the number of receptors 12 in the intracellular area increases. Therefore, an internalization state of the receptors from the cell membrane surface into the intracellular area in each cell can be efficiently detected with the first signal and the second signal.

Next, in step S17, the analysis device performs an information acquisition process of acquiring information indicating an internalization state of the receptors 12 through the cell membrane for each cell based on the first signal and the second signal acquired in step S16. Specifically, the analysis device acquires, for each cell, first information from the waveform of the first signal, and second information from the waveform of the second signal. The analysis device then acquires an "internalization ratio", an "internalization difference", or an "internalization value" as the information indicating an internalization state of the receptors 12 in the cell based on the acquired first information and the second information. The internalization ratio is a value obtained by dividing the first information by the second information, in other words, a ratio of the first information to the second information. The internalization difference is a value obtained by subtracting the second information from the first information, in other words, a difference between the first information and the second information. The internalization value is the first information. An internalization state of the receptors 12 in each cell can be smoothly detected by acquiring the information indicating the internalization state.

Here, the first information is the height of the waveform of the first signal, and the second information is the height of the waveform of the second signal. It is to be noted that the first information may be the area or width of the waveform of the first signal, and the second information may be the area or width of the waveform of the second signal. However, the first information and the second information are preferably the height of a signal waveform due to the reason described below with reference to FIGS. 4A to 4D.

Figure 4A:
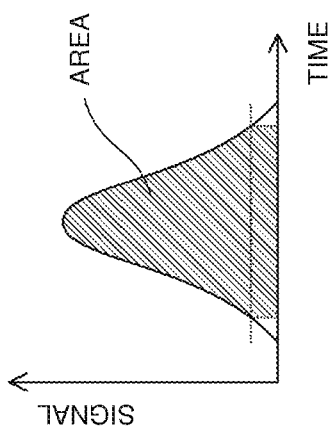
FIG. 4A is a schematic diagram illustrating a state where a cell without internalization of receptors is irradiated with a laser light according to a first embodiment.
Figure 4B:
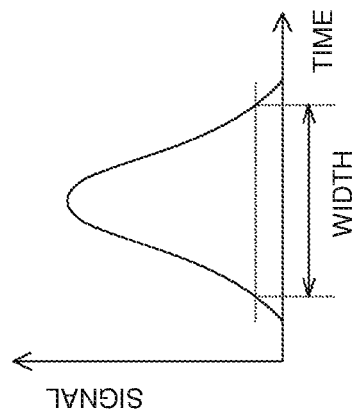
FIG. 4B is a schematic diagram illustrating a state where a cell with internalization of receptors is irradiated with a laser light according to a first embodiment.

FIG. 4A is a schematic diagram illustrating a state where the cell 10 illustrated in FIG. 3F is irradiated with a laser light. FIG. 4B is a schematic diagram illustrating a state where the cell 10 illustrated in FIG. 3C is irradiated with a laser light. As illustrated in FIGS. 4A and 4B, in a flow cytometer, the cell 10, which flows through a flow cell, is irradiated with a flat-shaped laser light.

Figure 4E:
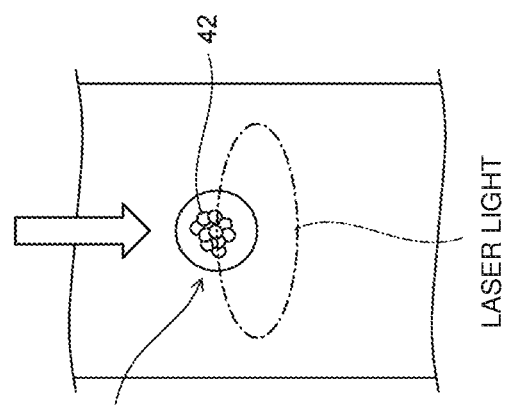
FIG. 4E is a schematic graph illustrating an area acquired from a signal waveform.
Figure 4F:
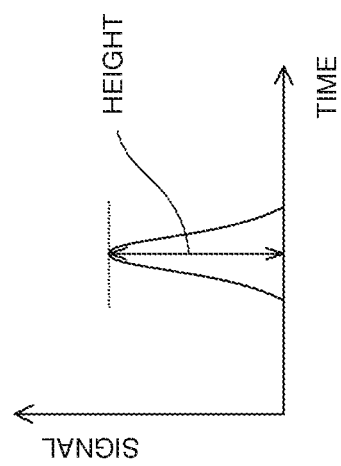
FIG. 4F is a schematic graph illustrating a width acquired from a signal waveform.
Figure 4C:
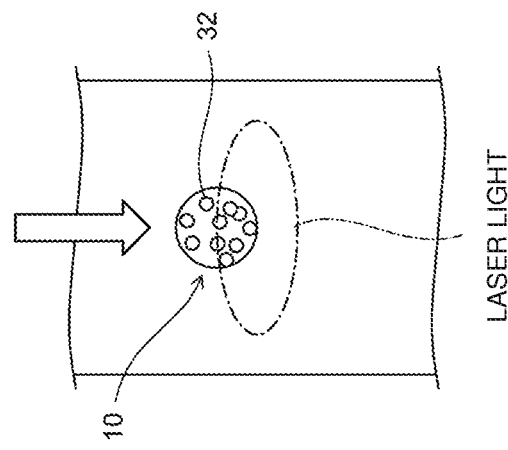
FIG. 4C is a schematic graph illustrating the waveform of a second signal acquired when a cell, such as in FIG. 4A, is irradiated with a laser light.

For the cell 10 illustrated in FIG. 4A, the receptors 12 are not internalized in the intracellular area, and thus the cell membrane surface is labeled with the labeling substance 32, and the intracellular area is not substantially labeled with the labeling substance 42. Therefore, when the cell 10 illustrated in FIG. 4A passes through an irradiation region of a laser light, fluorescence is generated from the labeling substances 32 which are widely distributed over the cell membrane surface, and fluorescence based on the labeling substances 42 is not substantially generated from the cell. In this case, the waveform of the second signal corresponding to the receptors 12 on the cell membrane surface has a shape as illustrated in FIG. 4C.

Figure 4D:
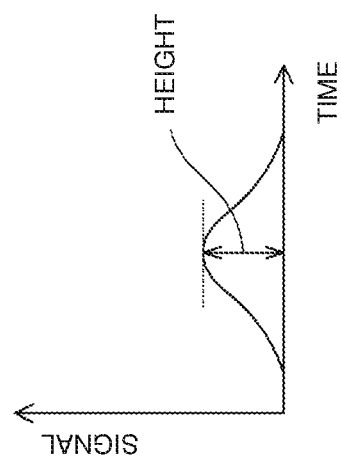
FIG. 4D is a schematic graph illustrating the waveform of a first signal acquired when a cell, such as in FIG. 4B, is irradiated with a laser light.

On the other hand, for the cell 10 illustrated in FIG. 4B, the receptors 12 has been internalized into the intracellular area from the cell membrane surface. Thus, in contrast to the case of FIG. 4A, the intracellular area is labeled with the labeling substance 42, and the cell membrane surface is less labeled with the labeling substance 32. In addition, the receptors 12 are internalized in the intracellular area in an aggregate state, and thus the labeling substances 42, which label the receptors 12 in the intracellular area, are also in an aggregate state. Therefore, when the cell 10 illustrated in FIG. 4B passes through an irradiation region of a laser light, fluorescence is generated from the labeling substances 42 in an aggregate state which are distributed in the intracellular area. Thus, in contrast to the case of FIG. 4A, fluorescence based on the labeling substance 32 is less generated from the cell. In this case, as illustrated in FIG. 4D, the waveform of the first signal corresponding to the receptors 12 in the intracellular area has a shape higher than the waveform of the second signal illustrated in FIG. 4C.

In this manner, in the cell 10 without internalization of receptors 12, the receptors 12 do not aggregate. Thus, although the second signal has a certain level of value according to the receptors 12 on the cell membrane surface, the height of the waveform of the second signal is not high as illustrated in FIG. 4C. On the other hand, in the cell 10 with internalization of receptors 12, the receptors 12 aggregate. Thus, the first signal has a certain level of value according to the receptors 12 in the intracellular area, and as illustrated in FIG. 4D, the height of the waveform of the first signal is higher than the height in FIG. 4C. Consequently, when the height of the signal waveform based on fluorescence is acquired as the first information and the second information, the values of the first information and the second information characteristically vary according to an internalization state of the receptors 12, and thus an internalization state of the receptors 12 in the intracellular area can be detected with high accuracy.

Also, in the binding in step S11 of FIG. 1, all the receptors 12 on the cell membrane surface not necessarily each binds to a binding substance 31, and, for instance, part, that is, approximately one-tenth of the receptors 12 remains unbound. In this case, in the labeling in step S13 of FIG. 1, the binding substance 41 may bind to a receptor 12 on the cell membrane surface, which does not bind to a binding substance 31, and the receptors 12 on the cell membrane surface may be labeled with the labeling substance 42. Also, the binding substance 41 may bind to a substance other than a receptor 12, and a substance other than a receptor 12 may be labeled with the labeling substance 42. The light generated from the labeling substance 42 that labels a receptor 12 on the cell membrane surface, and the light generated from the labeling substance 42 that labels a substance other than a receptor 12 are both noise.

However, as described above, since the receptors 12 are internalized in the intracellular area in an aggregate state, the aggregation degree of the labeling substances 42 that label substances other than the receptors 12 in the intracellular area is lower than the aggregation degree of the labeling substances 42 that label the receptors 12 in the intracellular area. Therefore, in a case where the height of a signal waveform is acquired as the first information, the first information provides a value that reflects aggregated labeling substances 42. Thus, a signal based on the receptors 12 internalized can be distinguished with high accuracy from a signal based on the noise generated from the cell membrane surface and noise generated from substances other than the receptors 12. Thus, even when a substance other than the receptors 12 in the intracellular area is labeled with the labeling substance 42, an internalization state of the receptors 12 in the intracellular area can be detected with high accuracy.

Here, as described above, the value of the first information and the value of the second information both characteristically vary according to an internalization state of the receptors 12. Therefore, the internalization state of receptors in the intracellular area tends to reflect on the internalization ratio, the internalization difference, and the internalization value. Thus, in step S17, when an internalization ratio, an internalization difference, or an internalization value is acquired as the information indicating an internalization state of the receptors 12 in each cell, an internalization state of the receptors 12 can be detected with high accuracy based on the information indicating the internalization state.

As described above, the first information and the second information are not limited to the height of a signal waveform. The first information and the second information may be the area of the signal waveform as illustrated in FIG. 4E or the width of the signal waveform as illustrated in FIG. 4F. However, in a case where the first information and the second information indicate the area or the width of a signal waveform, the value is unlikely to change according to internalization of receptors 12 for each of the first information and the second information, as compared with the case where the first information and the second information indicate the height of a signal waveform. Therefore, it is preferable that the first information and the second information indicate the height of a signal waveform.

Returning to FIG. 1, in step S18, the analysis device performs the determination process of determining whether internalization of receptors 12 through the cell membrane is present or absent for each cell based on the information indicating the internalization state acquired in step S17. Specifically, the analysis device determines whether internalization of receptors 12 through the cell membrane is present or absent for each cell by comparing information indicating an internalization state acquired for each cell with a predetermined threshold value.

For instance, in the case where the analysis device acquires an internalization ratio as information indicating an internalization state of the receptors 12 in each cell, when an internalization ratio is higher than or equal to a threshold value th1, internalization of a receptor 12 is determined to be present, and when an internalization ratio is lower than a threshold value th1, internalization of a receptor 12 is determined to be absent. Also, in the case where the analysis device acquires an internalization difference as information indicating an internalization state of the receptors 12 in each cell, when an internalization difference is higher than or equal to a threshold value th2, internalization of a receptor 12 is determined to be present, and when an internalization difference is lower than a threshold value th2, internalization of a receptor 12 is determined to be absent. Also, in the case where the analysis device acquires an internalization value as information indicating an internalization state of the receptors 12 in each cell, when an internalization value is higher than or equal to a threshold value th3, internalization of a receptor 12 is determined to be present, and when an internalization value is lower than a threshold value th3, internalization of a receptor 12 is determined to be absent.

In this manner, in the determination process in step S18, whether internalization of a receptor 12 in the intracellular area is present or absent is determined based on the information indicating an internalization state. Thus, presence or absence of internalization of a receptor 12 in the intracellular area can be smoothly determined. Also, in the determination process in step S18, whether internalization of a receptor 12 in the intracellular area is present or absent is determined by comparing the information indicating an internalization state with a predetermined threshold value. Thus, presence or absence of internalization of a receptor 12 in the intracellular area can be clearly determined.

Also, in a case where the receptor 12 is a target of a molecular target drug, when presence or absence of internalization of a receptor 12 in the intracellular area is determined, a result of the determination can be used for drug effect monitoring. For instance, in the case where a molecular target drug targeted to a receptor is administered to a subject, and the cell 10 in blood obtained from the subject is provided in the binding process in step S11, when presence or absence of internalization of a receptor 12 in the intracellular area is determined, the effect of the molecular target drug on the subject can be monitored.

For instance, when the receptor 12 as a target is an epidermal growth factor receptor (EGFR), a tyrosine kinase inhibitor (EGFR-TKI) is known as a molecular target drug. EGFR is present on a cell membrane. The epidermal growth factor receptor is activated, and thus differentiation or proliferation of cells occurs. However, occurrence of EGFR mutation involves in canceration, invasion, metastasis. Here, signal transmission necessary for proliferation of cancer cells can be blocked by inhibiting activation of EGFR using EGFR-TKI. Thus, proliferation of cancer cells can be suppressed. An internalization state of the receptors 12 in the intracellular area is determined in the cells in blood obtained from a subject to whom EGFR-TKI is administered. The internalization state serves as an index of activation of EGFR in each cell. Thus, the effect of EGFR-TKI on the subject can be monitored.

Also, a target receptor 12 is set to a receptor 12 for a bacterial disease or a receptor 12 for a viral disease, and it is thereby possible to know whether a subject suffers from a bacterial disease or a viral disease based on a result of the determination.

It is to be noted that a predetermined threshold value used in the determination process in step S18 is set based on information indicating an internalization state acquired based on a standard cell group with internalization of receptors 12 in the intracellular area, and information indicating an internalization state acquired based on a standard cell group without internalization of receptors 12 in the intracellular area. Thus, an appropriate threshold value can be set according to an environment in which an internalization state of the receptors 12 in the cell is detected.

Furthermore, in the determination process in step S18, the analysis device acquires the number of cells 10 in which a receptor 12 is internalized in the intracellular area, in other words, the number of cells 10 in which internalization of a receptor 12 is determined to be present, based on the presence or absence of internalization of a receptor 12 in the intracellular area in each cell. Also, in the determination process in step S18, the analysis device acquires the ratio of the cells in which internalization of a receptor 12 is determined to be present to the cells in which presence or absence of internalization of a receptor 12 in the intracellular area is determined. In this manner, the above-described evaluation of the effect of a molecular target drug and the later-described determination of presence or absence of extracellular stimulation can be smoothly made.

Furthermore, in the determination process in step S18, the analysis device determines presence or absence of extracellular stimulus based on a result of determination as to presence or absence of internalization of a receptor 12 in the intracellular area for each cell. For instance, based on the number of cells 10 in which a receptor 12 is internalized in the intracellular area, the analysis device determines extracellular stimulus is present in a case where the number is greater than or equal to a predetermined value, and determines extracellular stimulus is absent in a case where the number is less than a predetermined value. Alternatively, based on the ratio of the cells in which internalization of a receptor 12 is determined to be present, the analysis device determines extracellular stimulus is present in a case where the ratio is greater than or equal to a predetermined value, and determines extracellular stimulus is absent in a case where the ratio is less than a predetermined value. In a case where the combination of the receptor 12 and the ligand 20 is EGFR and EGF, and the presence or absence of extracellular stimulus is determined for each cell as described above, the presence or absence of EGF secreted due to differentiation or proliferation of cells can be smoothly determined.

In step S19, the analysis device performs a display process of displaying information on a determination result in step S18. Specifically, as the information on a determination result, the analysis device displays, on a display section, information indicating an internalization state of the receptors 12 in each cell, presence or absence of internalization of a receptor 12 in the intracellular area in each cell, the number of cells 10 in which a receptor 12 is internalized in the intracellular area, the ratio of the cells in which internalization of a receptor 12 is determined to be present to the cells in which presence or absence of internalization of a receptor 12 in the intracellular area is determined, and presence or absence of extracellular stimulus. Consequently, an operator can recognize the information on a determination result smoothly and visually. Also, an operator can smoothly and visually recognize a degree of internalization for each cell by referring to information indicating an internalization state displayed on the display section. The configuration of a screen on which a determination result is displayed is described later with reference to FIG. 10.

<Prior Check of Verification of First Embodiment>

Next, prior check of verification of a first embodiment conducted by the inventors before the verification of a first embodiment is described. In the prior check of verification of a first embodiment and the later-described verification of a first embodiment, internalization of EGFR in an intracellular area is verified using A549 cell having a high EGFR event rate of 99.9%.

1. Preparation

A human lung cancer cell line (A549) (deposited from JCRB) is prepared as a cell. Alexa 488-labeled EGF (Thermo Fisher Scientific: E13345) is prepared as a stimulating substance. Alexa 488-labeled EGF is obtained by labeling EGF which specifically binds to EGFR as a ligand with Alexa 488 which is a fluorescent substance. In addition, PRMI-1640 culture medium (SIGMA: R8758-500ML), fetal bovine serum (Hyclone: 515-83582), Antibiotic-Antimycotic (GIBCO: 15240-062), D-PBS (−) (Wako: 045-29795), glass bottom 6 well plate (Iwaki: 5816-006), paraformaldehyde (Wako: 160-16061), 0.05 w/v % trypsin-0.53 mmol/L EDTA (Wako: 204-16935), Hoechst33342 (Dojindo: 346-07951), CellHunt Orange (Setareh Biotech: 7138) are prepared.

2. Test Reagent Preparation

A cell culture medium (hereinafter referred to as a "complete culture medium") is produced by adding 50 mL of fetal bovine serum and 5 mL of Antibiotic-Antimycotic to 500 mL of RPMI-1640 culture medium. A cell culture medium (hereinafter referred to as a "starvation culture medium") is produced by adding 500 μL of fetal bovine serum and 5 mL of Antibiotic-Antimycotic to 500 mL of RPMI-1640 culture medium. A cell culture medium (hereinafter referred to as a "200 ng/mL of stimulus culture medium") is produced by adding Alexa 488-labeled EGF to the starvation culture medium to achieve a final concentration of 200 ng/mL. A cell culture medium (hereinafter referred to as a "2000 ng/mL of stimulus culture medium") is produced by adding Alexa 488-labeled EGF to the starvation culture medium to achieve a final concentration of 2000 ng/mL. Paraformaldehyde is dissolved by PBS to achieve a final concentration of 4 w/v %, then pH is adjusted to 7.4. CellHunt Orange is dissolved by DMSO to achieve a final concentration of 1 mM. A cell staining solution is produced by mixing CellHunt Orange solution, Hoechst33342 and PBS in the ratio of 1:1:998.

3. Procedure

A549 cell lines are cultivated in complete culture medium in accordance with the manufacturer recommended protocol. Cells which have been subcultured 30 times or less after purchase are used. The culture medium is removed using an aspirator from a 75 cm$^2$ flask in which A549 cells are cultivated, and the inside of the flask is washed once using 4 mL of PBS. 2 mL of 0.05% trypsin is added to the flask, and is left for 5 minutes at 37° C. and the cells are exfoliated. Then, 5 mL of complete culture medium is further added to the flask, the whole content is collected into a 15 mL centrifuge tube, to which centrifugation is applied at 300×g (1500 rpm) for 3 minutes. The supernatant fluid is removed, and cells are suspended in the complete culture medium to achieve a cell concentration of 5×10$^4$/mL, and sowed in 6-well glass plate at 2 mL/well, then are cultivated in an environment of 5% CO$_2$ at 37° C. overnight.

On the next day, the complete culture medium is removed, and the plate is washed using 1 mL of PBS. 2 mL of starvation culture medium is added, and starvation treatment is performed for 3 hours. The starvation culture medium is removed. A starvation culture medium, 200 ng/mL of stimulus culture medium, or 2000 ng/mL of stimulus culture medium in amount of 500 μL are added to respective wells, and are cultivated for 10 minutes at a room temperature. The added culture medium is removed, and the wells are washed 3 times using 1 mL of PBS, then 500 μL of 4% PFA-PBS is added and placed still for 15 minutes at a room temperature. After washing 3 times using 500 μL of PBS, 500 μL of a cell staining solution is added, and the cells are dyed for 15 minutes at a room temperature. After washing 3 times using 500 μL of PBS, 500 μL of PBS is added, and fluorescence generated from Alexa 488-labeled EGF and Hoechst33342 is captured using a confocal quantitative imaging cytometer. A captured image is analyzed and an internalization state of Alexa 488-labeled EGF is determined.

4. Determination Result

FIG. 5 illustrates a graph of a result of determination an internalization state of Alexa 488-labeled EGF, performed in the above-described procedure. The left end illustrates the case where starvation culture medium is added, in other words, the concentration of Alexa 488-labeled EGF is set to 0 ng/mL, and no stimulus is applied. The center illustrates the case where the concentration of Alexa 488-labeled EGF is set to 200 ng/mL, and low stimulus is applied. The right end illustrates the case where the concentration of Alexa 488-labeled EGF is set to 2000 ng/mL, and high stimulus is applied.

In each case, it is determined for multiple cells whether or not EGFR on a cell membrane surface is internalized in the intracellular area, based on the captured image acquired in the procedure 3 described above. When it is determined that EGFR is internalized in the intracellular area, the cell is determined to be positive. The number of positive cells out of the cells which are determination targets, in short, a positive rate is calculated. As illustrated in FIG. 5, in the case where the concentration of Alexa 488-labeled EGF is 0 ng/mL, the positive rate is substantially 0. In the case where the concentration of Alexa 488-labeled EGF is 200 ng/mL, the positive rate is 88.4%. In the case where the concentration of Alexa 488-labeled EGF is 2000 ng/mL, the positive rate is 96.8%.

In this manner, in the case where the concentration of Alexa 488-labeled EGF is 0 ng/mL, in other words, when no stimulus is applied, it has been verified that for nearly all cells, EGFR is not internalized in the intracellular area. Also, in the case where the concentration of Alexa 488-labeled EGF is 2000 ng/mL, in other words, when high stimulus is applied, it has been verified that for 95% or more of the cells, EGFR is internalized in the intracellular area. Thus, it has been found that a cell in which EGFR is not internalized in the intracellular area can be produced by setting the concentration of Alexa 488-labeled EGF to 0 ng/mL. Also, it has been found that a cell in which EGFR is internalized in the intracellular area can be produced by setting the concentration of Alexa 488-labeled EGF to 2000 ng/mL.

In the verification of a first embodiment described below, cells in which EGFR is not internalized in the intracellular area and cells in which EGFR is internalized in the intracellular area are produced based on the result of the prior check, and internalization of EGFR in the intracellular area is verified.

<Verification of First Embodiment>

For the cells in which EGFR is not internalized in the intracellular area and the cells in which EGFR is internalized in the intracellular area, the inventors determine the presence or absence of internalization of EGFR in the intracellular area by the technique of a first embodiment described with reference to FIG. 1.

1. Preparation

A human lung cancer cell line (A549) (deposited from JCRB) is prepared as a cell. Alexa 488-labeled EGF (Thermo Fisher Scientific: E13345) is prepared as a stimulating substance. In addition, PRMI-1640 culture medium (SIGMA: R8758-500ML), fetal bovine serum (Hyclone: 515-83582), Antibiotic-Antimycotic (GIBCO: 15240-062), D-PBS (–) (Wako: 045-29795), paraformaldehyde (Wako: 160-16061), Alexa647-labeled anti-EGFR antibody (Santa-Cruz: SC-120 AF647), PE-labeled anti-EGFR antibody (SantaCruz: SC-120 PE), bovine serum albumin (Sigma: A7906-50G), and Triton-X (Nacalai Tesque: 35501-15) are prepared.

Alexa647-labeled anti-EGFR antibody is obtained by labeling anti-EGFR antibody which specifically binds to EGFR with Alexa647 which is a fluorescent substance. In the verification, Alexa647-labeled anti-EGFR antibody corresponds to what the binding substance 31 and the labeling substance 32 illustrated in FIGS. 3A to 3F bind to each other. PE-labeled anti-EGFR antibody is obtained by labeling anti-EGFR antibody which specifically binds to EGFR with PE which is a fluorescent substance. In the verification, PE-labeled anti-EGFR antibody is what the binding substance 41 and the labeling substance 42 illustrated in FIG. 3C bind to each other.

2. Test Reagent Preparation

As in the preparation described above, complete culture medium is produced by adding 50 mL of fetal bovine serum and 5 mL of Antibiotic-Antimycotic to 500 mL of RPMI-1640 culture medium. As in the preparation described above, starvation culture medium is produced by adding 500 µL of fetal bovine serum and 5 mL of Antibiotic-Antimycotic to 500 mL of RPMI-1640 culture medium. A cell culture medium (hereinafter referred to as a "4000 ng/mL of stimulus culture medium") is produced by adding Alexa 488-labeled EGF to the starvation culture medium to achieve a final concentration of 4000 ng/mL. Paraformaldehyde is dissolved by PBS to achieve a final concentration of 4 w/v %, then pH is adjusted to 7.4. Washing liquid to be used below is produced by dissolving bovine serum albumin by PBS to achieve a final concentration of 1 w/v %.

3. Procedure

A549 cell lines are cultivated in complete culture medium in accordance with the manufacturer recommended protocol. Cells which have been subcultured 30 times or less after purchase are used. The complete culture medium is removed using an aspirator from a 150 cm$^2$ flask in which A549 cells are cultivated, and the inside of the flask is washed using 8 mL of PBS. 20 mL of starvation culture medium is added and starvation treatment is performed for 3 hours. The cells are exfoliated by a cell scraper and are made gone through a 50 µm mesh, and dispersed into single cells. The whole content is put into a 50 mL centrifuge tube. Centrifugation is applied at 300×g for 5 minutes, and the supernatant fluid is removed. Cells are suspended in the starvation culture medium to achieve a cell concentration of 4×10$^6$/mL. 250 µL of suspended cells is added to each of 1.7 mL tubes, 250 µL of starvation culture medium or 250 µL of 4000 ng/mL of stimulus culture medium is added to each tube, and are cultivated for 10 minutes at a room temperature. Consequently, in the tube to which 4000 ng/mL of stimulus culture medium is added, the concentration of Alexa 488-labeled EGF is 2000 ng/mL.

Centrifugation is applied to the tube at 300×g for 5 minutes, and the supernatant fluid is removed. A washing operation of adding 1 mL of washing liquid is repeated twice, then 500 µL of 4% PFA-PBS is added and placed still for 15 minutes at a room temperature. Centrifugation is applied to the tube at 300×g for 5 minutes, the supernatant fluid is removed, and a washing operation of adding 1 mL of washing liquid is repeated twice. Then, 500 µL of Alexa647-labeled anti-EGFR antibody solution prepared by PBS achieving a final concentration of 1 µg/mL is added and is dyed for 15 minutes. This procedure corresponds to the binding process illustrated in FIG. 1. Centrifugation is applied to the tube at 300×g for 5 minutes, the supernatant fluid is removed, and a washing operation of adding 1 mL of washing liquid is repeated twice, then 500 µL of Triton-X solution diluted with PBS, and membrane permeabilization is performed for 15 minutes. This procedure corresponds to the permeabilization process illustrated in FIG. 1. Centrifugation is applied to the tube at 300×g for 5 minutes, and the supernatant fluid is removed. A washing operation of adding 1 mL of washing liquid is repeated twice. Then, 500 µL of PE-labeled anti-EGFR antibody solution prepared by PBS achieving a final concentration of 1 µg/mL is added and is dyed for 15 minutes. This procedure corresponds to the labeling process illustrated in FIG. 1.

Centrifugation is applied to the tube at 300×g for 5 minutes, and the supernatant fluid is removed. A washing operation of adding 1 mL of washing liquid is repeated twice. Then, 300 μL of PBS is added. Fluorescence generated from the cells is measured by "BD Accuri" which is a general-purpose flow cytometer.

The signal based on the fluorescence generated from PE-labeled anti-EGFR antibody for labeling EGFR in an intracellular area corresponds to the first signal described in a first embodiment. The signal based on the fluorescence generated from Alexa647-labeled anti-EGFR antibody for labeling EGFR in an intracellular area corresponds to the second signal described in a first embodiment. The first information is set to the height of the waveform of the first signal, and the second information is set to the height of the waveform of the second signal. Then, an internalization ratio, an internalization difference, and an internalization value are acquired as the information indicating an internalization state of EGFR in each cell.

4. Verification Result

FIGS. 6A to 6F are each a graph illustrating a verification result in a first embodiment. FIGS. 6A to 6C are each a graph illustrating the internalization ratio, the internalization difference, and the internalization value acquired by the procedure 3 of the verification in a first embodiment. In FIGS. 6A to 6C, the left side of each graph illustrates a cell group in which the concentration of Alexa 488-labeled EGF to 0 ng/mL and no stimulus is applied, and the right side of each graph illustrates a cell group in which the concentration of Alexa 488-labeled EGF to 2000 ng/mL and sufficient stimulus is applied. In FIGS. 6A to 6C, the information indicating an internalization state of EGFR in each cell is illustrated by box-and-whisker plots extending in a lengthwise direction. In each of the box-and-whisker plots, the upper end and the lower end indicate a maximum value and a minimum value, respectively, and the horizontal line of the box portion indicates a median. The portion from the upper end of the box to the maximum value includes one fourth of all the cells, and the portion from the lower end of the box to the minimum value includes one fourth of all the cells.

As illustrated in FIG. 6A, in a case where the information indicating an internalization state of EGFR is an internalization ratio, a difference is found between distribution of cells without a stimulus and distribution of cells with a stimulus. As illustrated in FIG. 6B, in a case where the information indicating an internalization state of EGFR is an internalization difference, a difference is also found between distribution of cells without a stimulus and distribution of cells with a stimulus. As illustrated in FIG. 6B, in a case where the information indicating an internalization state of EGFR is an internalization value, a difference is also found between distribution of cells without a stimulus and distribution of cells with a stimulus.

Therefore, in the case of FIGS. 6A to 6C, it has been found that each cell can be properly classified into one of the cells without a stimulus and the cells with a stimulus by setting a cutoff. In other words, in the case of FIGS. 6A to 6C, it has been found that each cell can be properly classified into one of the cells in which EGFR is not internalized through a cell membrane, and the cells in which EGFR is internalized in an intracellular area.

Also, in the graphs of FIGS. 6A to 6C, a predetermined threshold value is set such that when each cell is classified according to the predetermined threshold value, a sensitivity and a specificity are maximized. For instance, in the case of FIG. 6A, when a predetermined threshold value th1 is set to maximize the sensitivity and the specificity, as illustrated in FIG. 6D, the predetermined threshold value th1, in short, the cutoff is 1.0. At this point, Area Under the Curve (AUC) is 0.986, the sensitivity is 97.8%, and the specificity is 84.3%.

Also, in the case of FIG. 6B, when a predetermined threshold value th2 is set to maximize the sensitivity and the specificity, as illustrated in FIG. 6E, the predetermined threshold value th2, in short, the cutoff is 317.832. At this point, AUC is 0.986, the sensitivity is 98.6%, and the specificity is 91.3%. Also, in the case of FIG. 6C, when a predetermined threshold value th3 is set to maximize the sensitivity and the specificity, as illustrated in FIG. 6F, the predetermined threshold value th3, in short, the cutoff is 596.4. At this point, AUC is 0.925, the sensitivity is 84.1%, and the specificity is 87.2%.

As illustrated in FIGS. 6D to 6F, it has been found that even when any one of the internalization ratio, the internalization difference, and the internalization value is used, the sensitivity and the specificity each can be set to a sufficiently high value. Therefore, it has been found that even when any one of the internalization ratio, the internalization difference, and the internalization value is used as the information indicating an internalization state of the receptors in a cell, a state of internalization of receptors in the cell can be detected with high accuracy. Also, as illustrated in FIGS. 6D to 6F, in cases where the internalization ratio and the internalization difference are used, AUC is 0.986 in each case and AUC is higher, as compared with the case where the internalization value is used. From this, it has been found that in cases where the internalization ratio and the internalization difference are used as the information indicating an internalization state of the receptors in a cell, a state of internalization of receptors in the cell can be detected with high accuracy.

It is to be noted that also in a case where the first information and the second information are set to the area of a signal waveform, as explained below, a target cell can be classified into one of the cells without a stimulus and the cells with a stimulus.

FIGS. 7A and 7B are each a graph illustrating the internalization ratio and the internalization difference in a case the first information and the second information are set to the area of a signal waveform. In the case illustrated in FIG. 7A, a difference is also found between distribution of cells without a stimulus and distribution of cells with a stimulus. Similarly, also in the case illustrated in FIG. 7B, a difference is found between distribution of cells without a stimulus and distribution of cells with a stimulus. Therefore, it has been found that also when the first information and the second information are set to the area of a signal waveform and the internalization ratio and the internalization difference are used, each cell can be properly classified into one of the cells without a stimulus and the cells with a stimulus by setting a cutoff. Thus, it has been found that also when the area of a signal waveform is used, a state of internalization of receptors in the cell can be detected.

<Device Configuration of First Embodiment>

The configuration of the cell information acquisition device based on the cell information acquisition method of a first embodiment is described.

Figure 8:
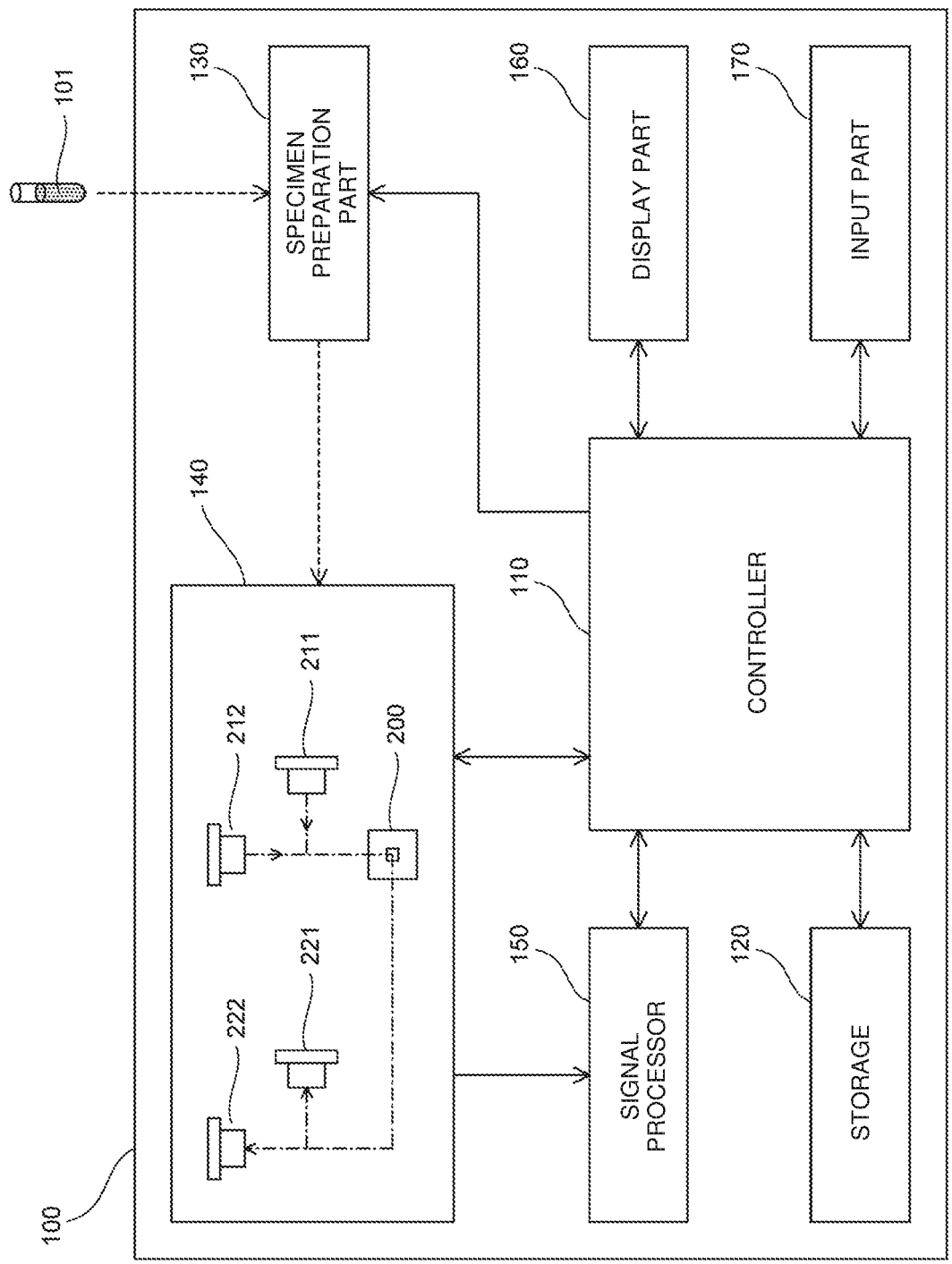
FIG. 8 is a block diagram illustrating the configuration of a cell information acquisition device according to the device configuration in a first embodiment.

As illustrated in FIG. 8, a cell information acquisition device 100 includes a controller 110, a storage 120, a specimen preparation part 130, a flow cytometer 140, a signal processor 150, a display part 160, and an input part 170.

The controller 110 includes a microcomputer, and a CPU. The storage 120 includes a RAM, a ROM, or a hard disk. The storage 120 stores a processing program, executed by the controller 110, and various data such as a signal value, and a numerical value. The controller 110 transmits and receives a signal to and from each unit of the cell information acquisition device 100 and controls each unit.

The specimen preparation part 130 prepares a specimen including a cell that has undergone each of steps S11 to S13 in accordance with steps S11 to S13 in FIG. 1 with the cells included in sample 101 and reagent connected to the specimen preparation part 130. The flow cytometer 140 causes a specimen to flow through a flow cell 200 in accordance with steps S14 to S16, and irradiates the specimen flowing through the flow cell 200 with the light from light sources 211, 212. Light receivers 221, 222 receive fluorescence generated from labeling substances 32, 42, and output a first signal based on the fluorescence generated from the labeling substance 42, and a second signal based on the fluorescence generated from the labeling substance 32. The detailed configuration of the flow cytometer 140 is described with reference to FIG. 9 later.

The signal processor 150 includes a circuit for processing a signal. The signal processor 150 acquires first information and second information from the waveforms of the first signal and the second signal outputted from the flow cytometer 140 for each cell. The controller 110 calculates information that indicates an internalization state of the receptors 12 in a cell, based on the first information and the second information acquired by the signal processor 150. In this manner, step S17 in FIG. 1 is performed by the signal processor 150 and the controller 110.

The controller 110 determines whether internalization of receptors 12 in the intracellular area is present or absent based on information indicating an internalization state of the receptors 12 acquired for each cell, in accordance with step S18 in FIG. 1. The controller 110 displays information on a determination result on the display part 160 in accordance with step S19 in FIG. 1. The display part 160 includes a display. Also, the controller 110 receives input from an operator via the input part 170. The input part 170 includes a mouse, a keyboard, and/or touch panel.

Figure 9:
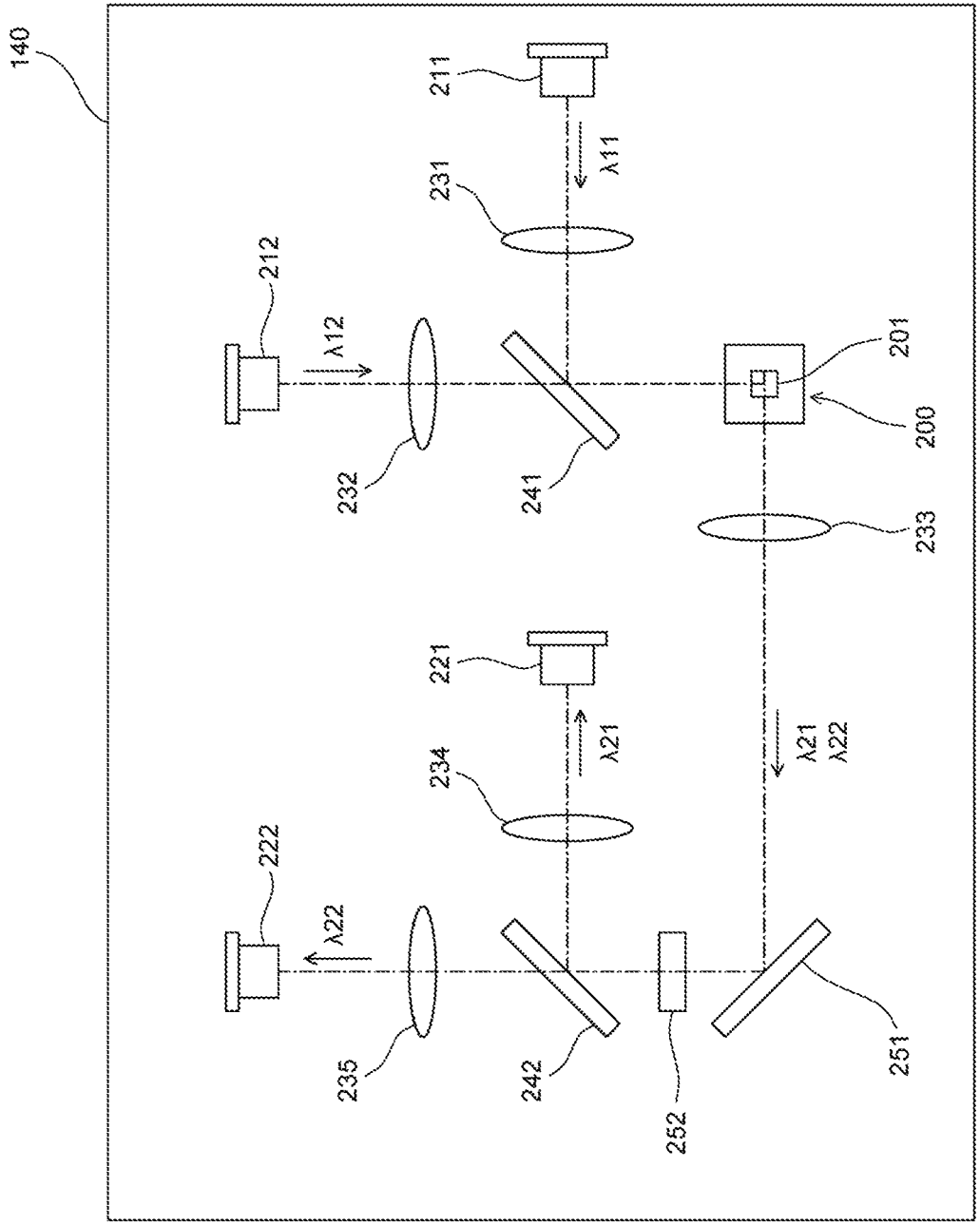
FIG. 9 is a schematic diagram illustrating the configuration of a flow cytometer according to the device configuration in a first embodiment.

As illustrated in FIG. 9, a flow cytometer 140 includes light sources 211, 212, light receivers 221, 222, collecting lenses 231 to 235, dichroic mirrors 241, 242, a mirror 251, and a filter 252. A flow path 201 is formed in the flow cell 200, and a specimen prepared by the specimen preparation part 130 flows through the flow path 20.

The light sources 211, 212 include a semiconductor laser light source. The light emitted from the light sources 211, 212 are laser lights having wavelengths $\lambda 11$, $\lambda 12$, respectively. The wavelength $\lambda 11$ is a wavelength of light for exciting fluorescence from the labeling substance 42 for labeling receptor 12 in an intracellular area. The wavelength $\lambda 12$ is a wavelength of light for exciting fluorescence from the labeling substance 32 for labeling receptor 12 in an intracellular area. The wavelength $\lambda 11$ and the wavelength $\lambda 12$ are mutually different wavelengths.

The collecting lenses 231, 232 collect the light emitted from the light sources 211, 212, respectively. The dichroic mirror 241 reflects light with the wavelength $\lambda 11$ and allows light with the wavelength $\lambda 12$ to pass through. The light with the wavelength $\lambda 11$ reflected by the dichroic mirror 241 and the light with the wavelength $\lambda 12$ that passes through the dichroic mirror 241 are emitted to a specimen which flows through the flow path 201 in an overlapping state. This allows fluorescence based on the labeling substances 32, 42 to be generated from a single cell simultaneously.

When a specimen flowing through the flow path 201 is irradiated with the light with the wavelength $\lambda 11$, fluorescence with a wavelength $\lambda 21$ is generated from the labeling substance 42. When the specimen flowing through the flow path 201 is irradiated with the light with the wavelength $\lambda 12$, fluorescence with a wavelength $\lambda 22$ is generated from the labeling substance 32. A collecting lens 233 collects fluorescence with wavelengths $\lambda 21$, $\lambda 22$ generated from the specimen flowing through the flow path 201. The mirror 251 reflects the fluorescence collected by the collecting lens 233. The filter 252 allows the fluorescence with wavelengths $\lambda 21$, $\lambda 22$ to pass through, and blocks unnecessary light. The dichroic mirror 242 reflects the fluorescence with the wavelength $\lambda 21$, and allows the fluorescence with the wavelength $\lambda 22$ to pass through. Collecting lenses 234, 235 collect the fluorescence with the wavelengths $\lambda 21$, $\lambda 22$, respectively.

The light receiver 221 receives the fluorescence with the wavelength $\lambda 21$, and outputs a signal in relation to the intensity of the received fluorescence as a first signal. The light receiver 222 receives the fluorescence with the wavelength $\lambda 22$, and outputs a signal in relation to the intensity of the received fluorescence as a second signal. The light receivers 221, 222 are, for instance, light detectors, and specifically, includes a photomultiplier tube. The first signal is a wave-like electrical signal such as a current or a voltage outputted by the light receiver 221, and the second signal is a wave-like electrical signal such as a current or a voltage outputted by the light receiver 222. In this manner, the flow cytometer 140 outputs the first signal based on the labeling substance 42 and the second signal based on the labeling substance 32.

Figure 10:
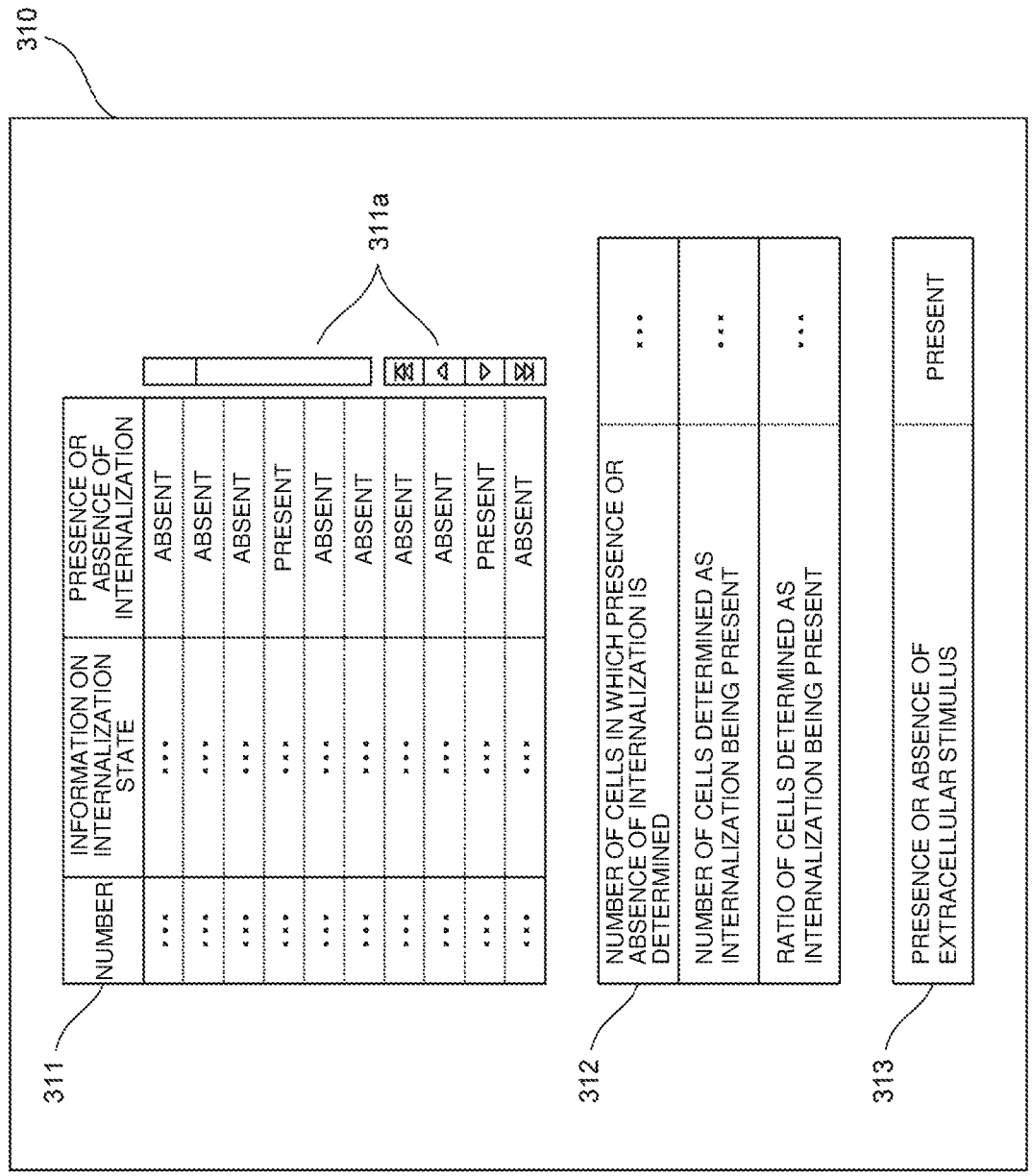
FIG. 10 is a schematic diagram illustrating the configuration of a screen displayed on a display section according to the device configuration in a first embodiment.

As illustrated in FIG. 10, in the display process illustrated in step S19 in FIG. 1, the controller 110 displays a screen 310 on the display part 160. The screen 310 includes lists 311 to 313.

The list 311 displays a serial number for identifying a cell individually, information indicating an internalization state of a receptor 12 in the cell, and presence or absence of internalization of the receptor 12 in the intracellular area in the cell. On the right side of the list 311, a scroll bar 311a for scrolling the content of display of the list 311 is provided. An operator can display information indicating the internalization state of all cells, and the presence or absence of internalization in each cell on the display area of the list 311 by operating the scroll bar 311a. The list 312 displays the number of cells in which the presence or absence of internalization in the intracellular area is determined, the number of cells in which the presence of internalization in the intracellular area is determined, and the ratio of cells in which the presence of internalization in the intracellular area is determined with respect to the total cells. The list 313 displays the presence or absence of extracellular stimulus. An operator can smoothly and visually recognize various kinds of information displayed on the lists 311 to 313 by referring to the screen 310.

Here, as described above, the portion of the receptor 12 recognized by the binding substance 41 is the same as the portion of the receptor 12 recognized by the binding substance 31. However, without being limited to this, the portion of the receptor 12 recognized by the binding substance 41 may be different from the portion of the receptor 12 recognized by the binding substance 31. In such a modification example, when the labeling process in step S13 in FIG. 1 is performed, as in the case illustrated in FIGS. 3C and 3F, the binding substance 31 binds to a receptor 12 on the cell membrane surface only. However, the binding substance 41 binds not only to a receptor 12 in the intracellular area, but also a receptor 12 on the cell membrane surface. In other words, both a receptor 12 in the intracellular area and a receptor 12 on the cell membrane surface are labeled with the labeling substances 42.

In this modification example, the light receiver 221 receives the fluorescence generated from the labeling substance 42 that labels of a receptor 12 on the cell membrane surface, and the fluorescence generated from the labeling substance 42 that labels of a receptor 12 in the intracellular area. Also, as in a first embodiment, the light receiver 222 receives the fluorescence generated from the labeling substance 32 that labels of a receptor 12 on the cell membrane surface. Therefore, in this modification example, the output signals of the light receivers 221, 222 are pre-adjusted so that a signal based on the fluorescence generated from the labeling substance 42 that labels of a receptor 12 on the cell membrane surface, and a signal based on the fluorescence generated from the labeling substance 32 that labels of a receptor 12 on the cell membrane surface have the same level. Thus, when a subtraction signal obtained by subtracting the output signal from the light receiver 222 from the output signal from the light receiver 221 is acquired, the subtraction signal indicates the signal based on the fluorescence generated from the labeling substance 42 that labels a receptor 12 in the intracellular area, in short, the first signal. Thus, also in this modification example, as in a first embodiment, the same effect can be obtained by performing the processing in and after step S17.

Second Embodiment

Figure 11:
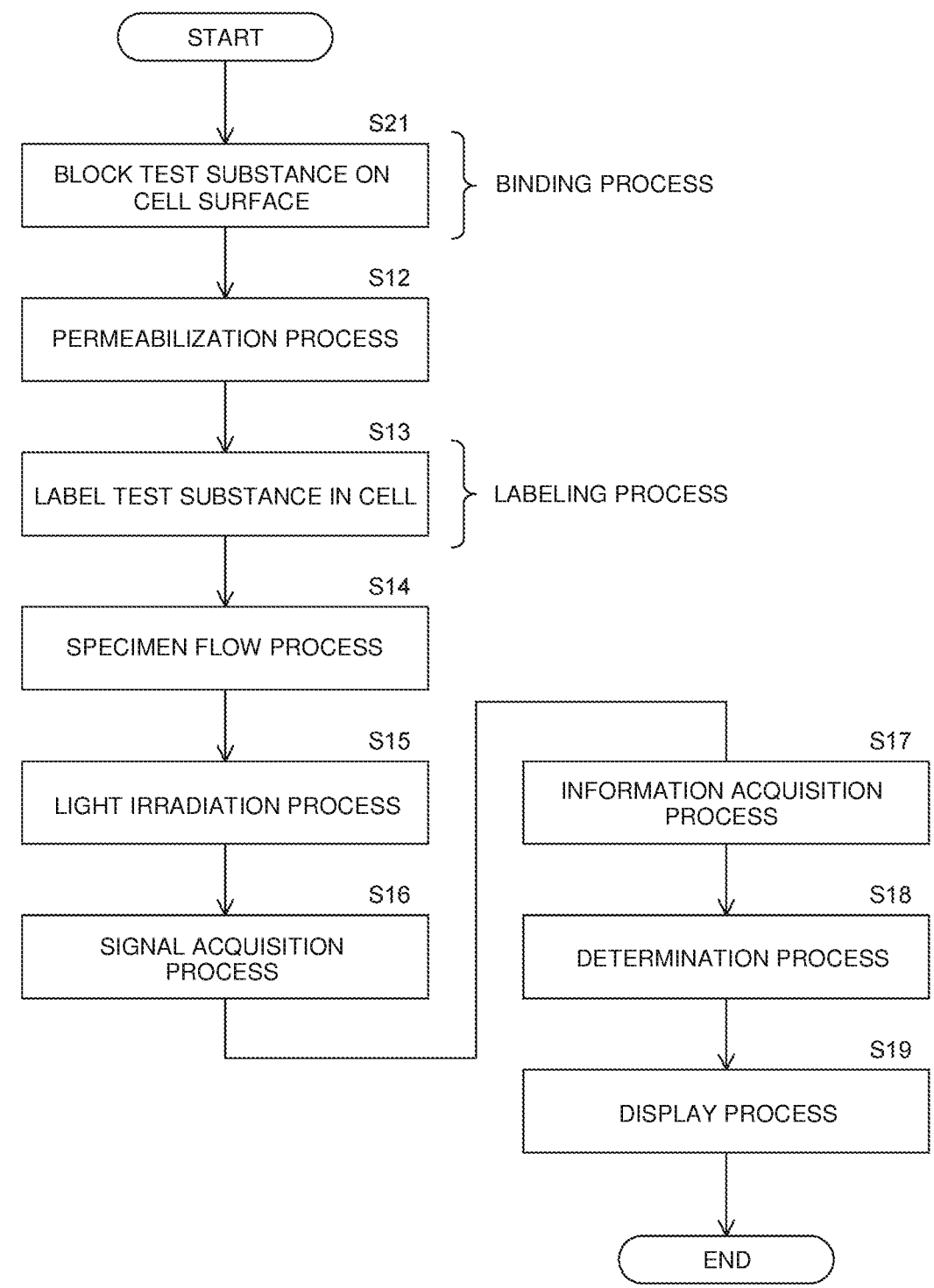
FIG. 11 is a flowchart illustrating a cell information acquisition method according to a second embodiment.

In a second embodiment, in the binding process, only the receptors 12 within each cell membrane are labeled by blocking the receptors 12 on the cell membrane surface. As illustrated in FIG. 11, in the processing process in a second embodiment, in comparison to the processing process in a first embodiment illustrated in FIG. 1, step S21 is added to replace step S11.

Hereinafter, the processing process in a second embodiment is described with reference to FIGS. 12A to 12F as needed. FIGS. 12A to 12C are each a diagram illustrating a process state of a cell 10 with internalization of receptors 12 with a stimulus applied to the cell. FIGS. 12D to 12F are each a diagram illustrating a process state of a cell 10 without internalization of receptors 12 with no stimulus applied to the cell.

In step S21, an operator performs binding process of blocking the receptors 12 on the cell membrane surface. Specifically, as illustrated in FIGS. 12A and 12D, the operator brings binding substances 31 into contact with the cell 10, and let each binding substance 31 bind to a receptor 12 on the cell membrane surface. The binding substance 31 is formed in the same manner as in a first embodiment. However, in contrast to a first embodiment, the binding substance 31 in a second embodiment is not labeled with a labeling substance 32. Due to the binding in step S21, the receptor 12 on the cell membrane surface binding to the binding substance 31 is in a state that does not allow binding to a binding substance 41.

In step S12, as in a first embodiment, the operator performs permeabilization process for a cell membrane 11. Thus, the cell membrane 11 of the cell 10 illustrated in FIGS. 12A and 12D are in a permeable state as illustrated with a dashed line in FIGS. 12B and 12E.

In step S13, as in a first embodiment, the operator performs the labeling process of labeling the receptors 12 in the intracellular area. For the cell 10 in which the receptor 12 is internalized in the intracellular area, as illustrated in FIG. 12C, the receptor 12 in the intracellular area is labeled with a labeling substance 42 via the binding substance 41 by the labeling process in step S13. On the other hand, for the cell 10 in which the receptor 12 is not internalized in the intracellular area, as illustrated in FIG. 12F, the cell membrane surface is not labeled with the labeling substance 42. Here, in a second embodiment, since the receptors 12 on the cell membrane surface are blocked in advance in step S21, the receptors 12 on the cell membrane surface are not labeled in step S13. Consequently, only the receptors 12 in the intracellular area are labeled.

In steps S14 to S16, as in a first embodiment, the operator performs a process of acquiring a first signal based on the fluorescence generated from the labeling substance 42 by a flow cytometry method. Acquisition of the first signal is performed in the same manner as in a first embodiment.

In step S21, S12 to S16 in a second embodiment, as in a first embodiment, the first signal based on the receptor 12 in the intracellular area can be acquired. Thus, also in a second embodiment, an internalization state of the receptor 12 in the intracellular area in each cell can be efficiently detected based on the first signal. However, in a second embodiment, a second signal based on the receptors 12 on the cell membrane surface is not acquired, and thus it is not possible to detect an internalization state based on both the first signal and the second signal as in a first embodiment. In order to detect an internalization state with high accuracy, it is preferable to acquire both the first signal and the second signal as in a first embodiment.

In step S17, the analysis device performs an information acquisition process of acquiring information indicating an internalization state of the receptor 12 in each cell based on the first signal acquired in step S16. Specifically, the analysis device acquires first information from the waveform of the first signal for each cell. As in a first embodiment, the first information is the height of the first signal. The analysis device then acquires an internalization value as the information indicating an internalization state of the receptors 12 in the cell. As in a first embodiment, the internalization value is the first information. Also in a second embodiment, as in a first embodiment, an internalization state of the receptor 12 can be detected based on the internalization value.

It is to be noted that also in a second embodiment, the first information may be the area or width of the waveform of the first signal. However, as described in a first embodiment, the height of the waveform of the first signal reflects the aggregated receptors 12 in the intracellular area, and thus it is preferable that the first information be the height of the waveform of the first signal.

In step S18, the analysis device performs a determination process of determining whether internalization of the receptor 12 in the intracellular area is present or absent for each cell based on the internalization value acquired in step S17. The determination based on an internalization value is performed in the same manner as in a first embodiment. Furthermore, in the determination in step S18, as in a first embodiment, the analysis device determines presence or absence of extracellular stimulus. In step S19, as in a first embodiment, the analysis device performs a display process It is to be noted that the device configuration of a second embodiment is the same as the device configuration of a first embodiment. However, the specimen preparation part 130 in a second embodiment performs the processing in steps S21, S12, S13 illustrated in FIG. 11. Also, since the second signal is not acquired in a second embodiment, the light source 212 and the light receiver 222 may be omitted in FIG. 9.

Third Embodiment

Figure 13:
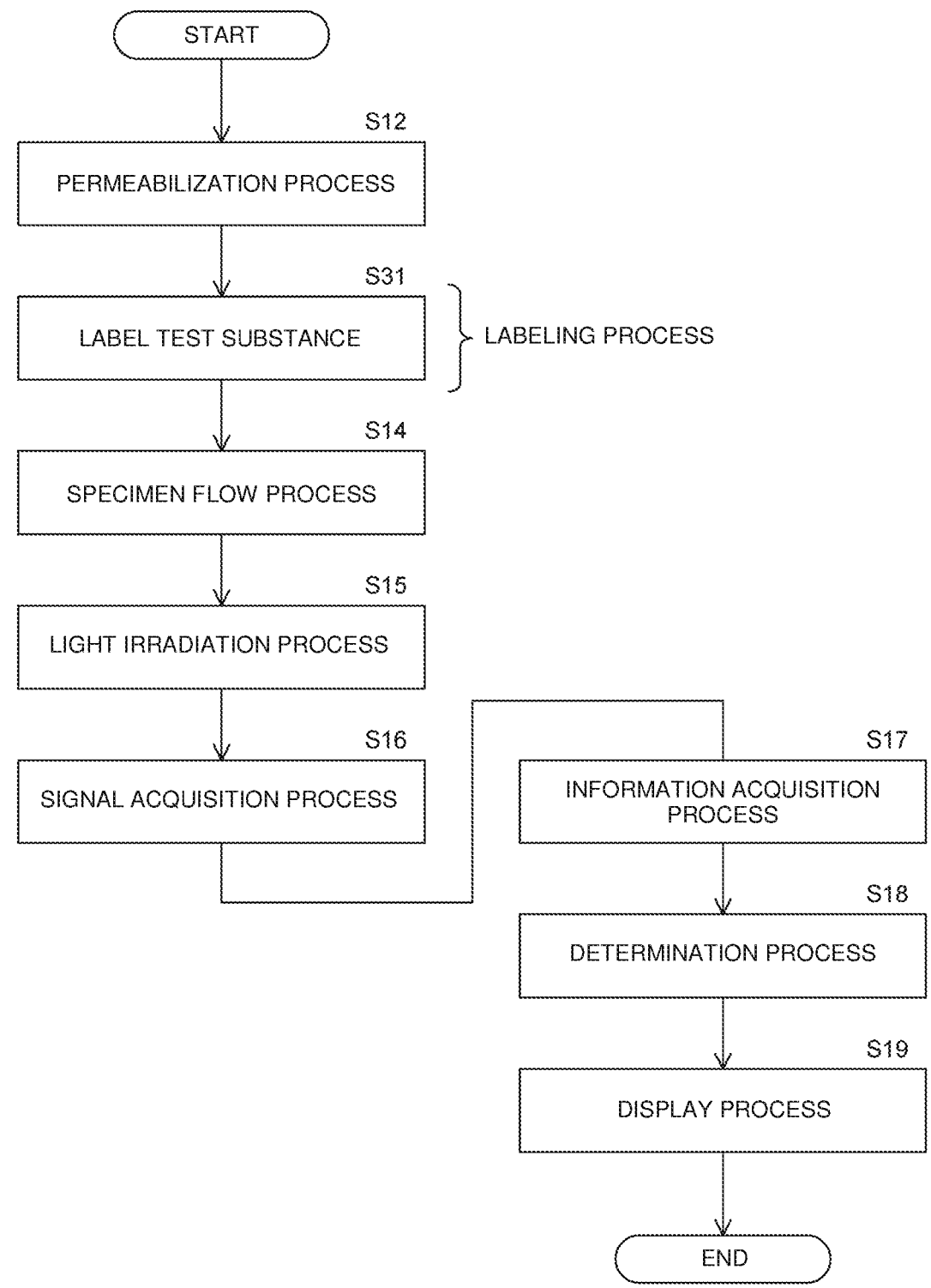
FIG. 13 is a flowchart illustrating a cell information acquisition method according to a third embodiment.

In a third embodiment, only the receptors 12 in an intracellular area are labeled by using a labeling substance that generates fluorescence in a physiological environment in the intracellular area. As illustrated in FIG. 13, in the processing process in a third embodiment, in comparison to the processing process in a second embodiment illustrated in FIG. 11, step S21 is omitted, and step S31 is added to replace step S13.

Hereinafter, the processing process in a third embodiment is described with reference to FIGS. 14A to 14E as needed. FIGS. 14A to 14C are each a diagram illustrating a process state of a cell 10 with internalization of receptors 12 caused with a stimulus applied to the cell. FIGS. 14D and 14E are each a diagram illustrating a process state of a cell 10 without internalization of receptors 12 caused with no stimulus applied to the cell.

In step S12, as in a second embodiment, an operator performs permeabilization process for a cell membrane 11. Thus, the cell membrane 11 of the cell 10, to which stimulus is applied, and the cell membrane 11 of the cell 10, to which no stimulus is applied, are in a permeable state as illustrated with a dashed line in FIGS. 14A and 14D.

In step S31, the operator performs a labeling process of labeling the receptors 12 using a binding substance 51. Specifically, as illustrated in FIGS. 14B and 14E, the operator brings the binding substance 51 labeled with a labeling substance 52 into contact with the cell 10, and let the binding substance 51 bind to a receptor 12 on the cell membrane surface. As with the binding substances 31, 41 in a first embodiment, a binding substance 51 is a substance bindable to the receptor 12. Also, at this point, the cell membrane 11 is in a permeable state, and thus the binding substance 51 labeled with the labeling substance 52 passes through the cell membrane 11 and enters the intracellular area. Thus, as illustrated in FIG. 14C, the binding substance 51 binds to a receptor 12 in the intracellular area. In this manner, the receptor 12 on the cell membrane surface and the receptor 12 in the intracellular area are labeled with the labeling substance 52 via the binding substance 51.

Here, the labeling substance 52 is configured to generate fluorescence in a physiological environment in the intracellular area. Specifically, the labeling substance 52 is configured to generate light according to pH in the intracellular area. In general, pH in an intracellular area is in a range of approximately 6.8 to 7.4. Also, pH outside a cell is, for instance, 6 or less and 8 or greater according to the composition of a reagent used for preparation of a specimen. Thus, the labeling substance 52, when being taken in an intracellular area, is in a state that allows generation of fluorescence. The labeling substance 52, when being not taken in the intracellular area, is in a state that does not allow generation of fluorescence. Thus, due to the labeling in step S31, the labeling substance 52 that labels a receptor 12 on the cell membrane surface is in a state that does not allow generation of fluorescence, and only the labeling substance 52 that labels a receptor 12 in the intracellular area is in a state that allows generation of fluorescence.

It is to be noted that the labeling substance 52 that generates fluorescence in a physiological environment in the intracellular area is not necessarily configured to generates fluorescence according to pH in the intracellular area. The labeling substance 52 that generates fluorescence in a physiological environment in the intracellular area may be configured to generate fluorescence according to a temperature or an oxygen partial pressure in the intracellular area. Alternatively, the labeling substance 52 may be configured to generate fluorescence by reaction with substances in the intracellular area, such as esterase.

In steps S14 to S16, as in a second embodiment, the operator performs a process of acquiring a signal based on the fluorescence generated from the labeling substance 52 by a flow cytometry method. As illustrated in FIG. 14C, for the cell 10 to which stimulus is applied, fluorescence is generated only from the labeling substance 52 that labels a receptor 12 in the intracellular area. As illustrated in FIG. 14E, for the cell 10 to which no stimulus is applied, fluorescence is not generated. Therefore, an internalization state of the receptor 12 in the intracellular area can be detected reliably by the signal based on the fluorescence generated from the labeling substance 52. The processing in steps S17 to S19 is performed in the same manner as in steps S17 to S19 in a second embodiment.

It is to be noted that when the cell membrane 11 is permeabilized in step S12, the cell transfers to a dead state. However, due to the difference between pH in the cell membrane and pH outside the cell, in order to set only the receptor 12 in the intracellular area in a state that allows generation of fluorescence, the cell has to maintain a living state. Therefore, in order to maintain a living state of the cells in the permeabilization process in step S12, the labeling process in step S31, and the processes in steps S14 to S16, all the processes have to be performed quickly, for example.

It is to be noted that the device configuration of a third embodiment is the same as the device configuration of a second embodiment. Specifically, the light source 212 and the light receiver 222 are omitted. In a third embodiment, fluorescence from the labeling substance 52 is excited by the light emitted from the light source 211. The light source 211 receives fluorescence generated from the labeling substance 52, and outputs a signal based on the intensity of the fluorescence generated from the labeling substance 52. The specimen preparation part 130 performs the processing processes in steps S12, S13 illustrated in FIG. 13.

Fourth Embodiment

Figure 15:
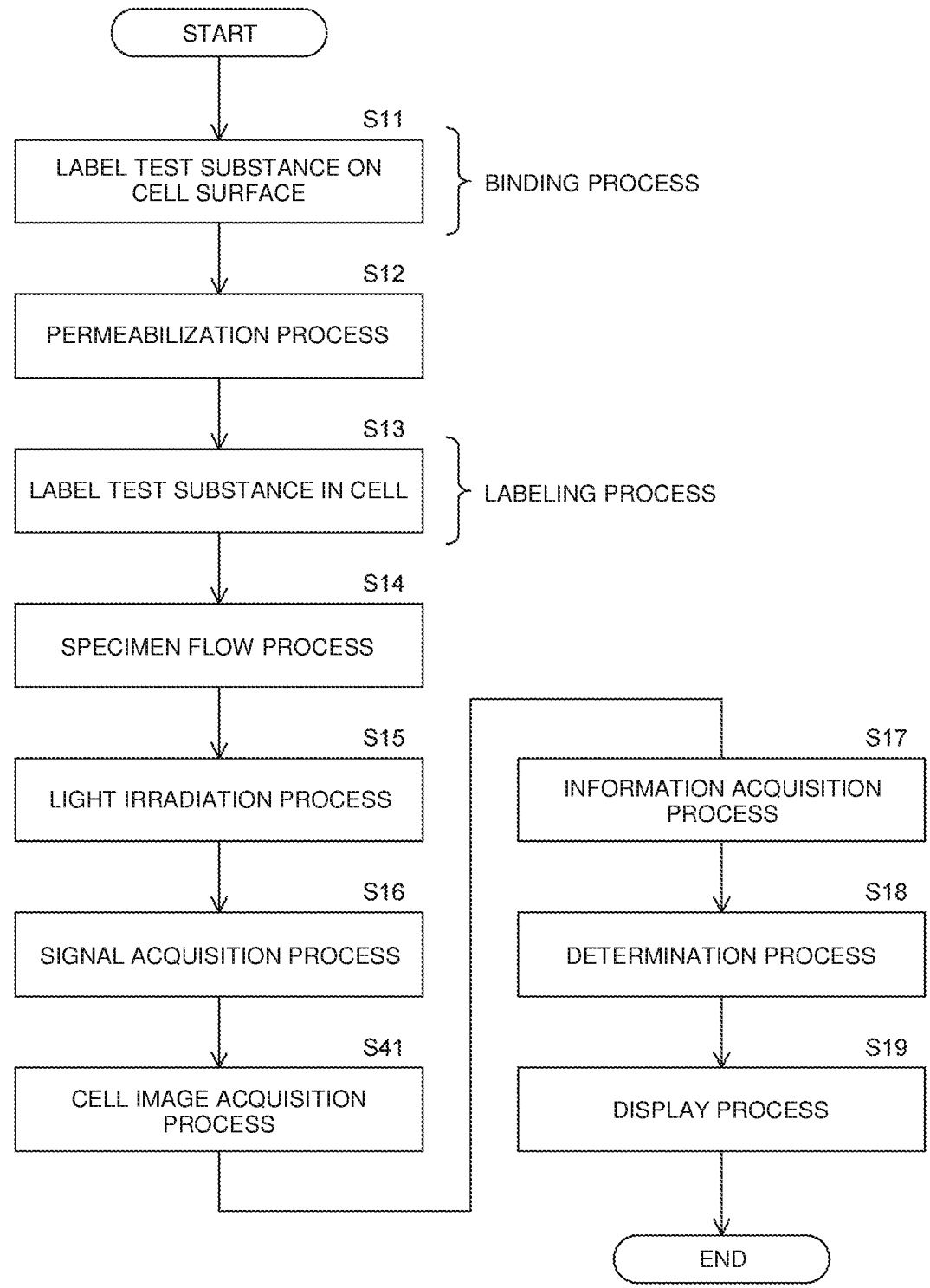
FIG. 15 is a flowchart illustrating a cell information acquisition method according to a fourth embodiment.

In a fourth embodiment, by a flow cytometry method, a signal is acquired, and an image of cells is acquired. As illustrated in FIG. 15, in the processing process in a fourth embodiment, in comparison to the processing process in a first embodiment illustrated in FIG. 1, step S41 is added to a subsequent stage of step S16.

As illustrated in FIG. 15, in steps S14 to S16 in a fourth embodiment, an operator performs a process of acquiring the first signal and the second signal by a flow cytometry method. Then in step S41, the operator performs a process of acquiring an image of cells using a flow cytometer.

Specifically, the flow cytometer receives the fluorescence generated from the labeling substances 32, 42 with a light receiver, and captures an image of cells included in a specimen which flows through the flow path of a flow cell with an image capturing part. The light receiver outputs the first signal and the second signal, and the image capturing part of the flow cytometer outputs a fluorescence image based on the fluorescence generated from the labeling substance 32, a fluorescence image based on the fluorescence generated from the labeling substance 42, and a bright-field image for each cell. In this manner, the operator acquires the first signal, the second signal, and the cell image using the flow cytometer.

The processing in steps S17 and S18 is performed in the same manner as in steps S17 and S18 in a first embodiment. In step S19, in addition to the same information as in a first embodiment, an analysis device displays a cell image acquired for each cell on the display part.

In a case where a cell image is acquired in this manner, for instance, an internalization state of the receptors 12 in the cell can be checked by referring to the cell image. Also, the presence or absence of internalization of the receptors 12 in the intracellular area in each cell can also be determined by analyzing the image. However, in a case where the presence or absence of internalization of the receptors 12 in the intracellular area is attempted to be determined by image analysis, and a large amount of samples are processed, the image analysis needs to be performed for a significant number of cells. In this case, an excessive load is applied to the analysis device that performs the image analysis. Therefore, it is preferable to detect an internalization state of the receptors 12 in each cell using the first signal and the second signal.

Figure 16:
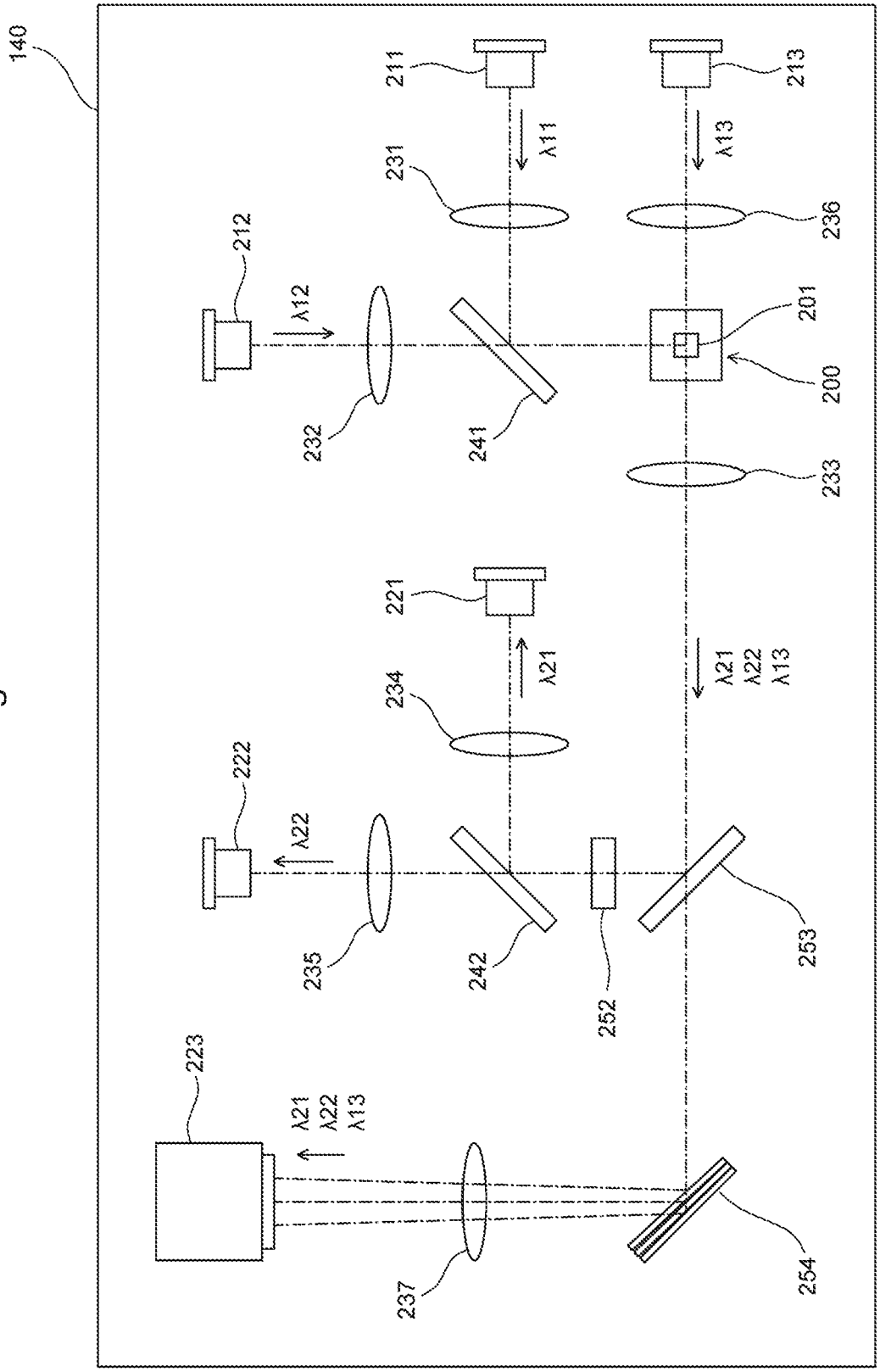
FIG. 16 is a schematic diagram illustrating the configuration of a flow cytometer according to the device configuration in a fourth embodiment.

In comparison to a first embodiment, in the device configuration of a fourth embodiment, the image capturing part is added to the inside of the flow cytometer 140. Specifically, as illustrated in FIG. 16, in comparison to the configuration illustrated in FIG. 9, the flow cytometer 140 includes a half mirror 253 instead of the mirror 251, and further includes a light source 213, collecting lenses 236, 237, an optical unit 254, and an image capturing part 223. Hereinafter, parts difference between the device configurations of the first and fourth embodiments are described.

The light source 213 includes a semiconductor laser light source. The light emitted from the light source 213 is a laser light with wavelength $\lambda 13$. The wavelength $\lambda 13$ is different from the wavelength $\lambda 11$ and the wavelength $\lambda 12$. The collecting lens 236 collects the light emitted from the light source 213. A specimen which flows through the flow path 201 is irradiated with the light having the wavelength $\lambda 11$, the light having the wavelength $\lambda 12$, and the light having the wavelength $\lambda 13$ in an overlapping state. When the specimen is irradiated with the light with the wavelength $\lambda 13$, the light passes through the cell. The light with the wavelength $\lambda 13$, which has passed through the cell, is used for generation of a bright-field image.

The light with the wavelength $\lambda 13$, which has passed through the cell, is collected by the collecting lens 233. The half mirror 253 allows half of the light which has passed through the collecting lens 233 to pass through, and reflects the rest half to a filter 252. The optical unit 254 is in the form of three dichroic mirrors combined. The three dichroic mirrors of the optical unit 254 reflect the fluorescence with the wavelength $\lambda 21$, the fluorescence with the wavelength $\lambda 22$, and the light with the wavelength $\lambda 13$ with a slightly different angle. The reflections are separated on a light receiving surface of the image capturing part 223. The collecting lens 237 collects the fluorescence with the wavelengths $\lambda 21$, $\lambda 22$, and the light with the wavelength $\lambda 13$. The image capturing part 223 includes, for instance, a time delay integration (TDI) camera. The image capturing part 223 receives the fluorescence with the wavelengths $\lambda 21$, $\lambda 22$, and the light with the wavelength $\lambda 13$, and outputs a fluorescence image corresponding to the fluorescence with the wavelengths $\lambda 21$, $\lambda 22$, and a bright-field image corresponding to the light with the wavelength $\lambda 13$ as the cell image.

Figure 17:
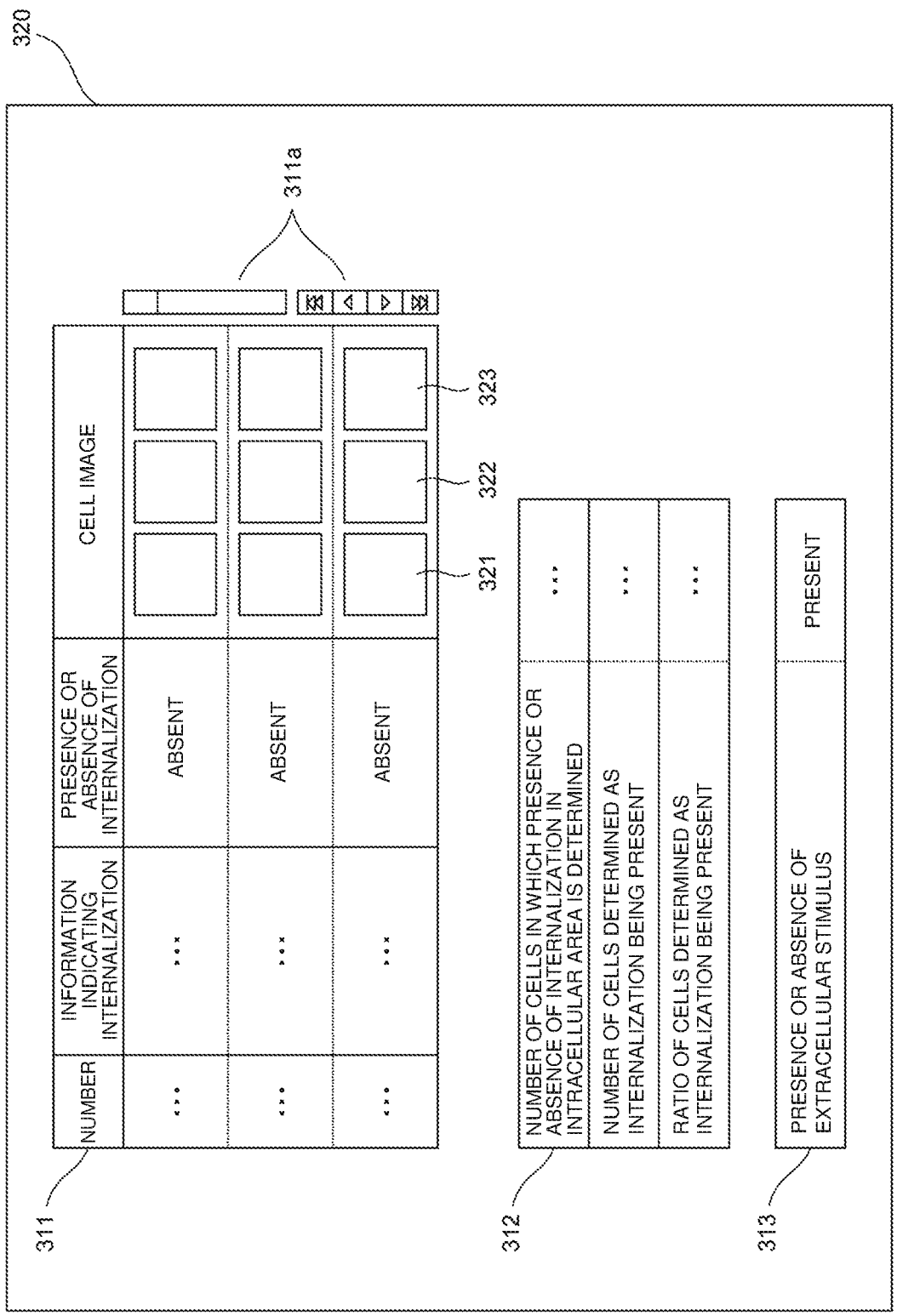
FIG. 17 is a schematic diagram illustrating the configuration of a screen displayed on a display section according to the device configuration in a fourth embodiment.
Figure 18B:
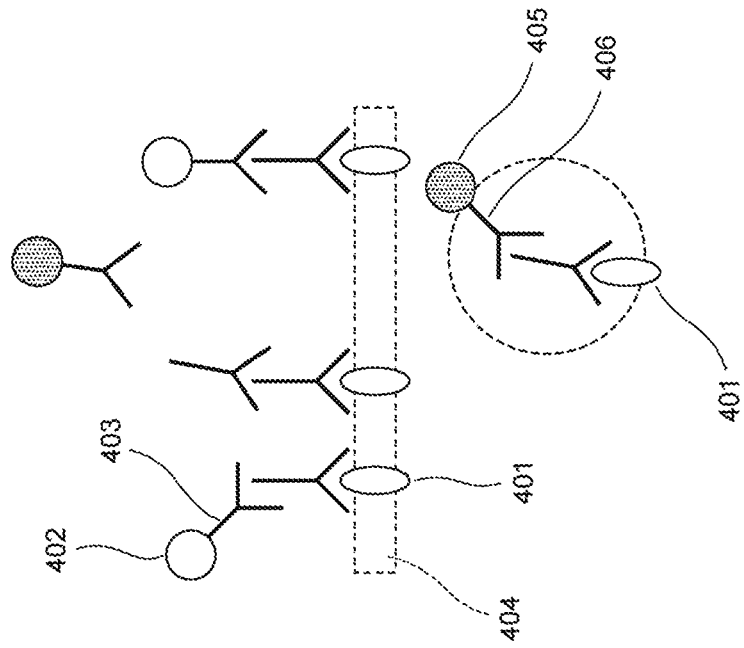
FIGS. 18A and 18B are schematic diagrams illustrating the configuration in related art.
Figure 18A:
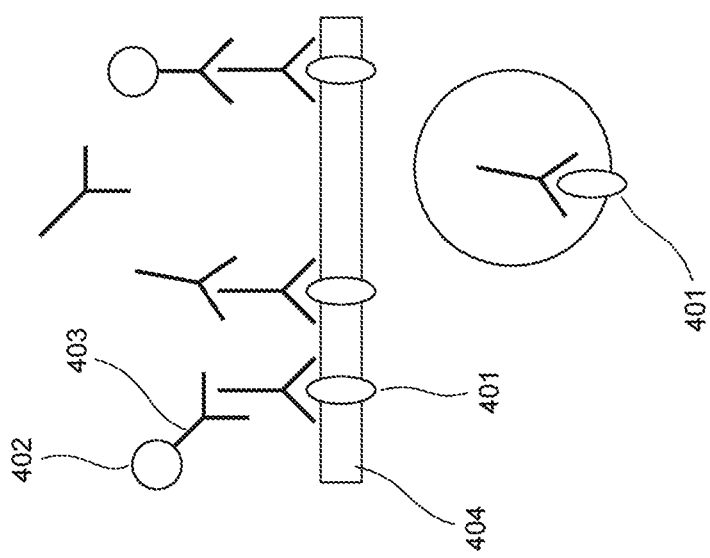

As illustrated in FIG. 17, in a fourth embodiment, in the display process illustrated in step S19 in FIG. 15, the controller 110 displays a screen 320 on the display part 160. In comparison to the screen 310 of a first embodiment illustrated in FIG. 10, the screen 320 displays a fluorescence image 321 based on the fluorescence with the wavelength $\lambda 21$, a fluorescence image 322 based on the fluorescence with the wavelength $\lambda 22$, and a bright-field image 323 based on the light with the wavelength $\lambda 13$ as the cell image on the list 311. The fluorescence images 321, 322, and the bright-field image 323 are displayed corresponding to each cell on the list 311. Also in this case, an operator can display information indicating the internalization states of all cells, the presence or absence of internalization, and the cell image on the display area of the list 311 by operating the scroll bar 311a. Also in a fourth embodiment, an operator can smoothly and visually recognize various kinds of information including the cell image displayed on the lists 311 to 313 by referring to the screen 310.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:
1. A cell information acquisition method comprising:
contacting a cell with a first binding substance labeled with a first labeling substance, the first binding substance being bindable to a receptor on a cell membrane surface of a cell;
permeabilizing the cell membrane of the cell after the contacting with the first binding substance;
contacting the cell with a second binding substance labeled with a second labeling substance after the permeabilizing, the second binding substance being bindable to a receptor having been internalized through the cell membrane into an intracellular area of the cell, thereby preparing a cell mixture;
causing the cell mixture including the cell to flow through a flow path after the contacting with the second binding substance;
irradiating the cell included in the cell mixture flowing through the flow path with light;
acquiring a signal based on light with a first wavelength generated from the first labeling substance and a signal based on light with a second wavelength different from the first wavelength generated from the second labeling substance in the cell irradiated with light, and
acquiring a ratio or a difference between information on a height of a waveform of the acquired signal based on the light with the first wavelength, and information on a height of a waveform of the acquired signal based on the light with the second wavelength, wherein the ratio or difference provides an indication of an internalization state of the receptor having been internalized through the cell membrane into the intracellular area of the cell, and
counting cells having the ratio or difference greater than a threshold as cells in which the receptor has been internalized through the cell membrane into the intracellular area.

2. The cell information acquisition method according to claim 1, wherein the signal based on the light with the first wavelength comprises an electrical signal outputted by a light receiver.

3. The cell information acquisition method according to claim 1, wherein the signal based on the light with the second wavelength comprises an electrical signal outputted by a light receiver.

4. The cell information acquisition method according to claim 1, further comprising displaying information that indicates the internalization state of the receptor having entered through the cell membrane into the intracellular area of the cell.

5. The cell information acquisition method according to claim 1, further comprising determining whether internalization of the receptor having entered through the cell membrane into the intracellular area of the cell is present or absent for the cell based on information that indicates the internalization state of the receptor having entered through the cell membrane into the intracellular area of the cell.

6. The cell information acquisition method according to claim 5, wherein the cell comprises a cell in blood obtained from a subject to which a molecular target drug targeted to the receptor is administered.

7. The cell information acquisition method according to claim 5, wherein the determining comprises comparing the information that indicates the internalization state with a predetermined threshold value.

8. The cell information acquisition method according to claim 5, further comprising displaying the presence or absence of internalization of the receptor having entered through the cell membrane into the intracellular area of the cell determined for the cell in the determining.

9. The cell information acquisition method according to claim 5, wherein the determining comprises acquiring the number of cells in which the internalization of the receptor having entered through the cell membrane into the intracellular area of the cell is present.

10. The cell information acquisition method according to claim 9, further comprising
displaying the acquired number of the cells in which the internalization of the receptor having entered through the cell membrane into the intracellular area of the cell is present.

11. The cell information acquisition method according to claim 9, wherein the determining comprises determining whether extracellular stimulation is present or absent based on the number of the cells in which the internalization of the receptor having entered through the cell membrane into the intracellular area of the cell is present.

12. The cell information acquisition method according to claim 5, wherein the determining comprises acquiring a ratio of the cells in which the internalization of the receptor having entered through the cell membrane into the intracellular area of the cell is present to cells in which presence or absence of internalization of the receptor having entered through the cell membrane into the intracellular area of the cell is determined.

13. The cell information acquisition method according to claim 1, further comprising acquiring an image of the cell included in the cell mixture flowing through the flow path.

14. A cell information acquisition method comprising:
contacting a cell with a first binding substance labeled with a first labeling substance, the first binding substance being bindable to a receptor on a cell membrane surface of a cell;
permeabilizing the cell membrane of the cell after the contacting with the first binding substance;
contacting the cell with a second binding substance labeled with a second labeling substance after the permeabilizing, the second binding substance being bindable to a receptor having been internalized through the cell membrane into an intracellular area of the cell, thereby preparing a cell mixture;
causing the cell mixture including the cell to flow through a flow path after the contacting with the second binding substance;
irradiating the cell included in the cell mixture flowing through the flow path with light;
acquiring a signal based on light with a first wavelength generated from the first labeling substance and a signal based on light with a second wavelength different from the first wavelength generated from the second labeling substance in the cell irradiated with light, and
acquiring a ratio or a difference between information on an area of a waveform of the acquired signal based on the light with the first wavelength, and information on an area of a waveform of the acquired signal based on the light with the second wavelength, wherein
the ratio or difference provides an indication of an internalization state of the receptor having entered through the cell membrane into the intracellular area of the cell, and
counting cells having the ratio or difference greater than a threshold as cells in which the receptor has been internalized through the cell membrane into the intracellular area.

15. A cell information acquisition method comprising:
contacting a cell with a first binding substance labeled with a first labeling substance, the first binding substance being bindable to a receptor on a cell membrane surface of a cell;
permeabilizing the cell membrane of the cell after the contacting with the first binding substance;
contacting the cell with a second binding substance labeled with a second labeling substance after the permeabilizing, the second binding substance being bindable to a receptor having been internalized through the cell membrane into an intracellular area of the cell, thereby preparing a cell mixture;
causing the cell mixture including the cell to flow through a flow path after the contacting with the second binding substance;
irradiating the cell included in the cell mixture flowing through the flow path with light;
acquiring a signal based on light with a first wavelength generated from the first labeling substance and a signal based on light with a second wavelength different from the first wavelength generated from the second labeling substance in the cell irradiated with light, and
acquiring a ratio or a difference between information on a first width of a waveform of the acquired signal based on the light with the first wavelength, and information on a second width of a waveform of the acquired signal based on the light with the second wavelength, wherein
the ratio or difference indicates an internalization state of the receptor having entered through the cell membrane into the intracellular area of the cell, and
counting cells having the ratio or difference greater than a threshold as cells in which the receptor has been internalized through the cell membrane into the intracellular area.

* * * * *